(12) United States Patent
Howgill

(10) Patent No.: US 11,497,866 B2
(45) Date of Patent: Nov. 15, 2022

(54) TRIGGER MECHANISM FOR AN INHALER

(71) Applicant: KINDEVA DRUG DELIVERY L.P., St. Paul, MN (US)

(72) Inventor: Stephen J. Howgill, Leicestershire (GB)

(73) Assignee: Kindeva Drug Delivery L.P., St. Paul, MN (US)

( * ) Notice: Subject to any disclaimer, the term of this patent is extended or adjusted under 35 U.S.C. 154(b) by 802 days.

(21) Appl. No.: 16/331,213

(22) PCT Filed: Sep. 5, 2017

(86) PCT No.: PCT/US2017/050057
§ 371 (c)(1),
(2) Date: Mar. 7, 2019

(87) PCT Pub. No.: WO2018/048790
PCT Pub. Date: Mar. 15, 2018

(65) Prior Publication Data
US 2019/0275271 A1 Sep. 12, 2019

(30) Foreign Application Priority Data
Sep. 7, 2016 (GB) ...................................... 1615183

(51) Int. Cl.
*A61M 15/00* (2006.01)
(52) U.S. Cl.
CPC ...... *A61M 15/0091* (2013.01); *A61M 15/009* (2013.01); *A61M 15/0021* (2014.02); *A61M 15/0068* (2014.02)

(58) Field of Classification Search
CPC .. A61M 15/009–0098; A61M 15/0021; A61M 15/0068–0081; A61M 16/20
See application file for complete search history.

(56) References Cited

U.S. PATENT DOCUMENTS 3,456,646 A * 7/1969 Phillips ............. A61M 15/0095
128/200.23
4,298,023 A 11/1981 McGinnis
(Continued)

FOREIGN PATENT DOCUMENTS

CN 102264422 A 11/2011
CN 104302197 A 1/2015
(Continued)

OTHER PUBLICATIONS

International Search report for PCT International application No. PCT/US17/50057 dated Nov. 7, 2017, 3 pages.

*Primary Examiner* — Elliot S Ruddie
(74) *Attorney, Agent, or Firm* — Mueting Raasch Group

(57) ABSTRACT

A breath-responsive metered dose inhaler having a trigger mechanism for triggering delivery of a medicament and a trigger mechanism chassis for locating the trigger mechanism within the inhaler, the trigger mechanism including a breath responsive member moveable upon inhalation of the user from a primed position in which the inhaler is prevented from delivering medicament, to a triggered position in which the medicament is delivered to the user, a spring which is flexible along its longitudinal axis, wherein the spring is configured to bias the breath responsive member from its triggered position to its primed position by flexure along its longitudinal axis.

13 Claims, 25 Drawing Sheets

(56) References Cited

U.S. PATENT DOCUMENTS

| | | |
|---|---|---|
| 5,347,998 A | 9/1994 | Hodson |
| 5,447,150 A | 9/1995 | Bacon et al. |
| 2004/0237961 A1 | 12/2004 | Snow et al. |
| 2006/0037611 A1* | 2/2006 | Mahon .............. A61M 15/0091 128/203.15 |
| 2006/0150971 A1 | 7/2006 | Lee |
| 2008/0156321 A1* | 7/2008 | Bowman .......... A61M 15/0091 128/200.23 |
| 2012/0017903 A1 | 1/2012 | Von Schuckmann |
| 2012/0132203 A1 | 5/2012 | Hodson |
| 2013/0192615 A1 | 8/2013 | Tucker et al. |
| 2013/0192616 A1 | 8/2013 | Tucker et al. |
| 2013/0228178 A1 | 9/2013 | Rogers, Jr. |
| 2015/0297859 A1 | 10/2015 | Spandorfer et al. |

FOREIGN PATENT DOCUMENTS

| | | | |
|---|---|---|---|
| CN | 105342790 A | 2/2016 | |
| EP | 0254548 | 1/1986 | |
| EP | 2606892 | 6/2013 | |
| WO | WO 1999-047199 | 9/1999 | |
| WO | WO 2008/110584 A2 | 9/2008 | |
| WO | WO 2013/188609 A1 | 12/2013 | |
| WO | WO 2014-139912 | 9/2014 | |
| WO | WO 2015-006292 | 1/2015 | |
| WO | WO-2015150734 A1 * | 10/2015 | ........ A61M 15/0026 |
| WO | WO 2016-005728 | 1/2016 | |
| WO | WO 2018-048797 | 3/2018 | |

* cited by examiner

TRIGGER MECHANISM FOR AN INHALER

CROSS REFERENCE TO RELATED APPLICATIONS

This application is a national stage filing under 35 U.S.C. 371 of PCT/US2017/050057, filed Sep. 5, 2017, which claims the benefit of GB Application No.1615183.9, filed Sep. 7, 2016, the disclosure of which is incorporated by reference in its/their entirety herein.

FIELD

The present application relates to a breath-actuated trigger mechanism for use in a dose release firing system for inhalers, particularly medicinal inhalers. The application also relates to inhalers and in particular to medicinal inhalers containing a medicament container.

BACKGROUND

Delivery of aerosolized medicament to the respiratory tract for the treatment of respiratory and other diseases has been done using pressurised metered dose inhalers (pMDI), dry powder inhalers (DPI) and nebulizers. pMDI inhalers are familiar to many patients who suffer from either asthma or from chronic obstructive pulmonary disease (COPD). pMDI devices often comprise an aluminum canister, sealed with a metering valve, which contains a medicament formulation. Generally, the medicament formulation is pressurized and contains either fine particles of one or more medicinal compounds suspended in a liquefied hydrofluoroalkane (HFA) propellant, or a solution of one or more medicinal compounds dissolved in a propellant/co-solvent system. Formulations incorporating drugs in both solution and suspension form are also known.

Dry powder inhalers are sometimes described as "breath-actuated" because many of them utilise the energy of a patient's inhaled breath to release a dose of powdered medicament, usually admixed with a suitable carrier powder, for the patient to inhale directly. However, some DPIs are designed to dispense the dose actively by releasing a separate energy source to the powder, upon activation of a mechanism by the patient's inhalation.

In a conventional pulmonary pMDI, the sealed canister is provided to the patient in an actuator. The actuator is conventionally a generally L-shaped plastic molding comprising a generally cylindrical vertical tube that surrounds the canister plus a generally horizontal tube that forms a patient portion (e.g., a mouthpiece or nosepiece) that defines an inspiration (or inhalation) orifice. To use such an inhaler, the patient exhales, places the patient port into a body cavity (e.g., a mouth or nose) and then inhales to draw air through the inspiration orifice. Many such inhalers are of the pulmonary "press-and-breathe" type, where the patient must press down on the protruding end of the canister to operate the metering valve to release a metered dose of medicament from the canister into the inhaled air stream and thence through the mouthpiece into their lungs. This can require coordination of timing of inhalation and dose release if the emerging cloud of aerosolized medicament is to be taken far enough into the lungs to provide maximum therapeutic benefit. If the patient releases the dose before inspiratory flow has been established, then a proportion of the drug may be lost in the mouthpiece or the patient's mouth. Conversely, if released much after the start of inhalation, then the deeper regions of the lungs might already be full of air and not penetrated by the following bolus of released medicament aerosol.

Spacer devices have previously been devised which fit onto the mouthpiece of a pMDI to reduce the velocity of the emergent plume of medicament aerosol and to provide a volume in which it can expand and its propellant can evaporate more completely. This serves to avoid some of the problems of coordination and the tendency for high throat deposition caused by excessively fast drug particle inhalation. However, spacer devices are bulky and can retain an excessive proportion of the drug on their walls, thereby reducing the dose that reaches the patient. Spacer devices can also be highly sensitive to electrostatic charge, which can often be strongly affected by the way in which they are washed or dried.

To overcome what can be quite a challenge for some patients, some pMDI device designs have been created that employ automatic breath-actuated triggering, releasing a dose only in response to the patient's inhaled breath. The AUTOHALERT™ metered dose inhaler, available from 3M Company, St. Paul, Minn., USA, and the EASIBREATHE™ inhaler, available from Teva Pharmaceutical Industries Ltd., Israel, are two such pMDI devices that use breath-actuation to attempt to better coordinate dose release with inhalation. Many other inhaler breath-actuated mechanisms have been proposed, but tend to have one or more weaknesses or disadvantages, for example high component counts (and hence high manufacturing costs), complexity (which can give rise to difficulties of assembly and/or complex dimensional tolerance stack-ups, etc.), performance issues (it is difficult to balance sensitivity (a light triggering force) against stability at rest and/or prior to inhalation) and/or excessive size and/or a less familiar or more awkward overall inhaler shape.

The issue of cost is a particular concern when considering price-sensitive markets such as those for generic drug products or in Asia. The embodiments of the present invention seek to provide breath actuation at a manufacturing cost low enough to make it highly attractive even in price sensitive markets.

Even though breath-actuated inhalers can be a useful aid in achieving coordination between inhalation and medicament dose release, some of the existing devices employ mechanical breath-actuation systems that may need to be tightly toleranced to be both stable and yet also sensitive. The nature of stored energy mechanical breath-actuation systems can be such that a large load of several tens of Newtons (e.g., held in a compression spring) needs to be held back (i.e., prevented from release) by a latching mechanism that has to be unlatched using only the force of the patient's breath (e.g., 1 Newton, from a reasonably sized vane). That requires a large 'mechanical advantage', whereby a small force can release a much larger one. For example, pMDI metering valves can require over 40 N to fire them, meaning that a compression spring to drive them needs to provide in excess of that force even after it has moved the valve by around 2-3 mm or so: i.e., it needs to provide >40 N even at the point where it has already unloaded by 2-3 mm from its compressed state at which the firing mechanism was primed (or 'cocked').

SUMMARY

The present disclosure describes a breath-responsive metered dose inhaler having a trigger mechanism for triggering delivery of a medicament and a trigger mechanism chassis for locating the trigger mechanism within the inhaler, the trigger mechanism including:

a breath responsive member moveable upon inhalation of the user from a primed position in which the inhaler is prevented from delivering medicament, to a triggered position in which the medicament is delivered to the user, a spring which is flexible along its longitudinal axis, wherein the spring is configured to bias the breath responsive member from its triggered position towards its primed position by flexure along its longitudinal axis.

Advantageously, the provision of a spring that biases the breath responsive member by flexure along its longitudinal axis ensures a substantially consistent spring force throughout movement of the breath responsive member from its triggered position to its primed position. This is achieved by virtue of the relatively consistent spring rate of a spring under longitudinal flexure across a sufficiently large displacement to allow complete movement of the breath responsive member from its triggered position to its primed position. This is in contrast, for example, to a coil spring in compression, which only delivers a relatively constant spring rate over a short range of displacement. Thus the spring of the present disclosure is able to deliver a sufficiently low biasing load when the breath responsive member is in its primed position so as not to impair the sensitivity of the trigger mechanism whilst also delivering a consistent return biasing force as the breath responsive member moves from its primed position to its triggered position. This is important as the breath responsive member must open fully so as to allow effective delivery of the medicament to the user.

Preferably, the spring is a helical spring.

Advantageously, a helical spring delivers the advantageous spring rate and range of travel features set out above.

Preferably, the flexure is a straightening flexure.

Preferably the inhaler trigger mechanism comprises a toggle mechanism comprising the breath responsive member, wherein the spring is attached to the toggle mechanism.

Preferably, the spring has its first end attached to the breath responsive member and a longitudinally opposing second end attached to the trigger mechanism chassis.

More preferably, the helical spring is constrained by the trigger mechanism chassis to include a pre-load by way of a bend when the breath responsive member is in its primed position, and a further bend giving rise to an increased biasing force in its triggered position.

Advantageously, the pre-load in the primed position ensures that the trigger mechanism returns to the rest position. This in turn ensures consistent co-ordination between the user's inhaled breath and triggering of the inhaler.

In a preferred attachment configuration, the spring is attached to the trigger mechanism chassis by an interference fit of the second end of the spring inside a sleeve of the trigger mechanism chassis or outside a boss of the trigger mechanism chassis.

Preferably the spring is attached to the breath responsive member by an interference fit of the first end of the spring inside a sleeve of the breath responsive member or outside a boss of the breath responsive member.

Preferably, the breath responsive member is constrained to pivot about a fixed axis and the spring engages the breath responsive member close to the fixed axis.

Preferably, the breath responsive member is a vane.

Other features and aspects of the present disclosure will become apparent by consideration of the detailed description and accompanying drawings.

DETAILED DESCRIPTION

Before describing embodiments in accordance with the present invention (with reference to FIGS. 2 to 25), an embodiment of a conventional pMDI device will be described with reference to FIG. 1.

Figure 1:
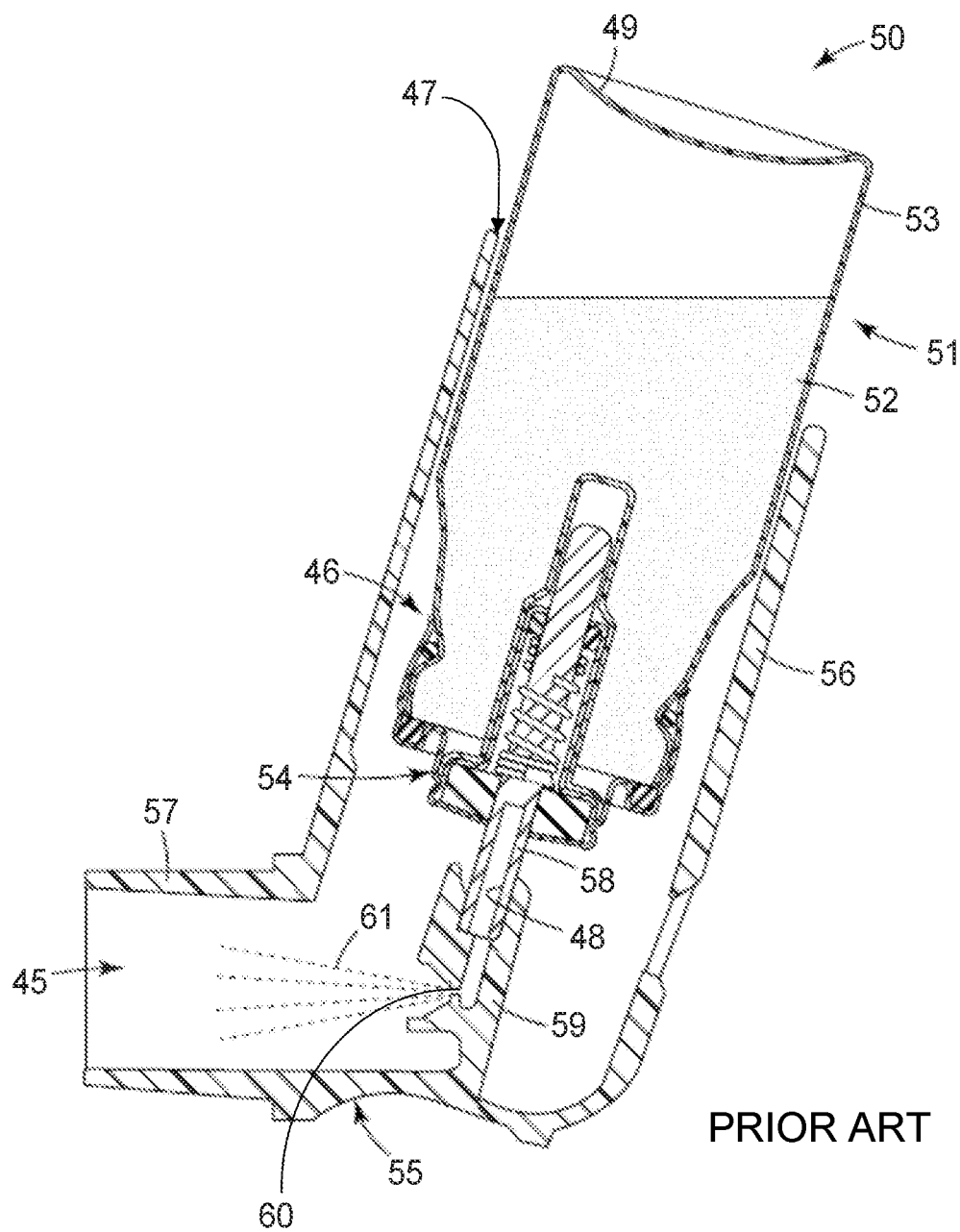
FIG. 1 is a side cross-sectional view of a conventional pressurized metered dose inhaler (pMDI) of the prior art.

FIG. 1 illustrates a conventional pressurized metered dose inhaler (pMDI) 50 comprising a canister 51 containing a medicament formulation 52, the canister comprising a can 53 sealed at a crimp 46 with a metering valve 54. The canister 51 sits within a housing (or "actuator") 55 comprising a tubular sleeve portion 56 having an open end 47 dimensioned to receive the canister 51 and from which its base 49 can protrude, and a portion in the form of a patient port 57 (e.g., in the form of a mouthpiece) that defines an inspiration orifice (or an air outlet) 45. Such a patient port of an inhaler is sometimes referred to herein as a "mouthpiece" for simplicity. However, it should be understood that such mouthpieces can instead be configured to be nosepieces of nasal inhalers and that the present disclosure can equally apply to nasal inhalers even where not specifically mentioned herein. The open upper end of the housing 55 can define an aspiration orifice, or an air inlet, and the air outlet 45 can define an inhalation orifice, or an air outlet.

A stem portion 58 protrudes from the metering valve 54 and is located and retained by friction in a stem socket 59 formed as an integral part of the housing 55. A spray orifice 60 is formed in the stem socket 59, and provides a passage for fluid communication between the stem portion 58 and the air outlet 45. In use, a patient places the patient port (e.g., mouthpiece) 57 into a body cavity (e.g., mouth) and then inhales through it while at the same time pressing downwards on the base 49 of the canister 51. The pressing force serves to move the canister 51 downwards relative to the stem portion 58. That relative movement serves to isolate a metered dose of medicament formulation from the bulk formulation in the canister 51 and then to discharge it via a hollow bore 48 formed in the stem portion 58. The discharged dose then passes along the fluid passageway through the stem socket 59 and emerges via a spray orifice in the form of a fine respirable spray 61 that passes through the patient port 57 into the patient's body cavity (e.g., oral cavity and/or nasal cavity) and thence into their respiratory passages, thereby treating their disease.

One important aspect of such a conventional pMDI device 50 that has the potential to limit its efficacy is, in particular, its need for good patient coordination between the timing of the start of inhalation and the moment at which the canister 51 is pressed downwards. The load is applied to a medicament source either directly by the patient, often by thumb or forefinger, or by compression or tensioning of a spring against the medicament source, or by some other energy source. Coordination is a challenge for a high proportion of patients, leading to poor and often highly varying efficacy of medicament administration.

As shown in FIGS. 14-15 and 18-25, embodiments of the present disclosure comprise breath-actuated trigger mechanisms that incorporate a toggle mechanism.

Figure 2:
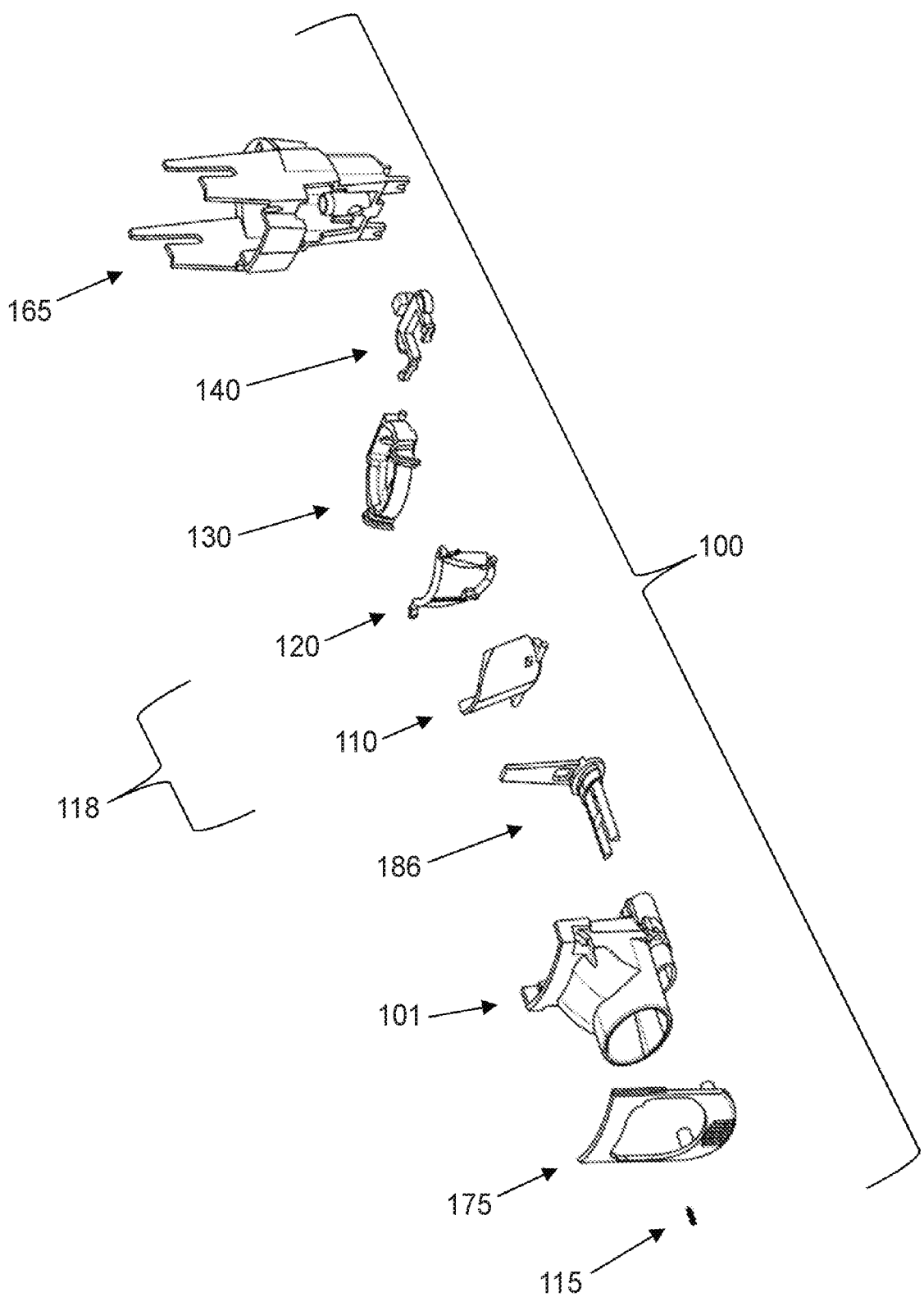
FIG. 2 is an exploded view of the components of a first embodiment of a breath-actuated trigger mechanism of the present disclosure.

FIG. 2 shows components of a first embodiment of breath-actuated trigger system of the present disclosure (shown in their assembled state in FIG. 14), comprising a lower body component 165, a trigger mechanism chassis 101, a breath responsive member in the form of vane 110, a toggle link 120, an actuation arm 130, a vane spring 115, a fascia component 175, a flow governor support component 186 and a button component 140. This includes components 118 of the toggle mechanism 119 (shown in FIG. 14).

Figure 3:
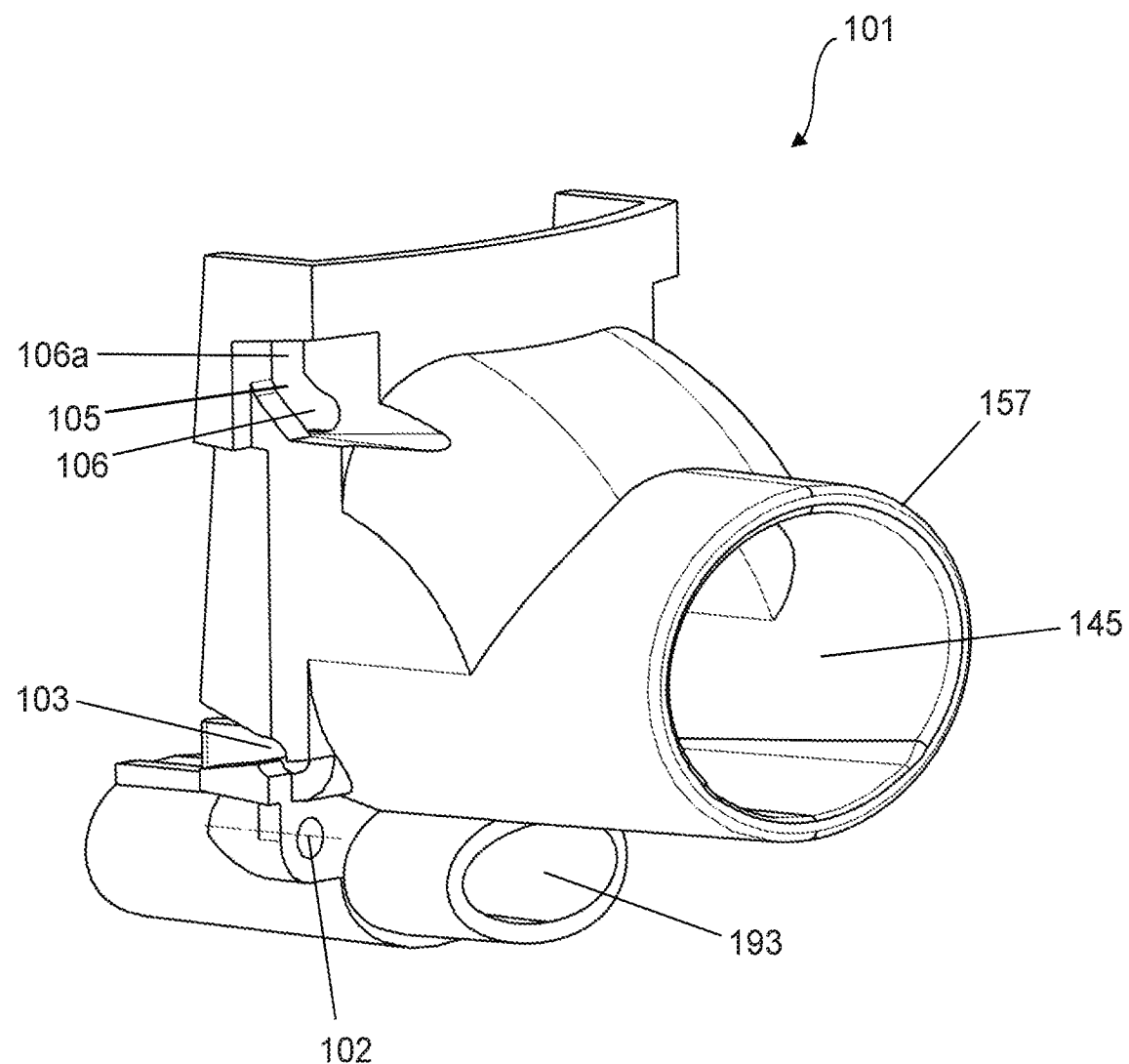
FIG. 3 is a front isometric view of the trigger mechanism chassis of FIG. 2.
Figure 4:
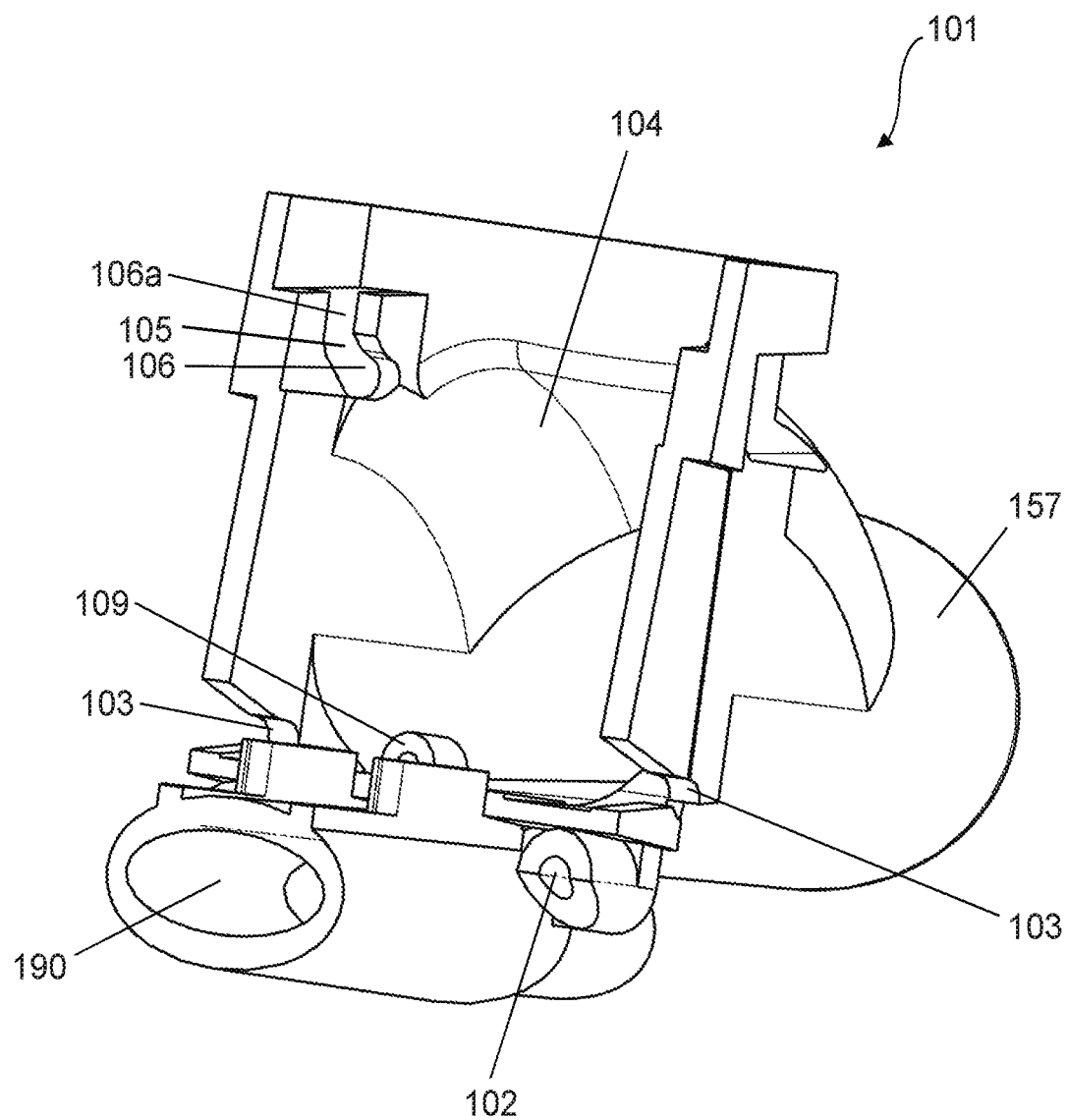
FIG. 4 is a rear isometric view of the trigger mechanism chassis of FIG. 2.
Figure 5:
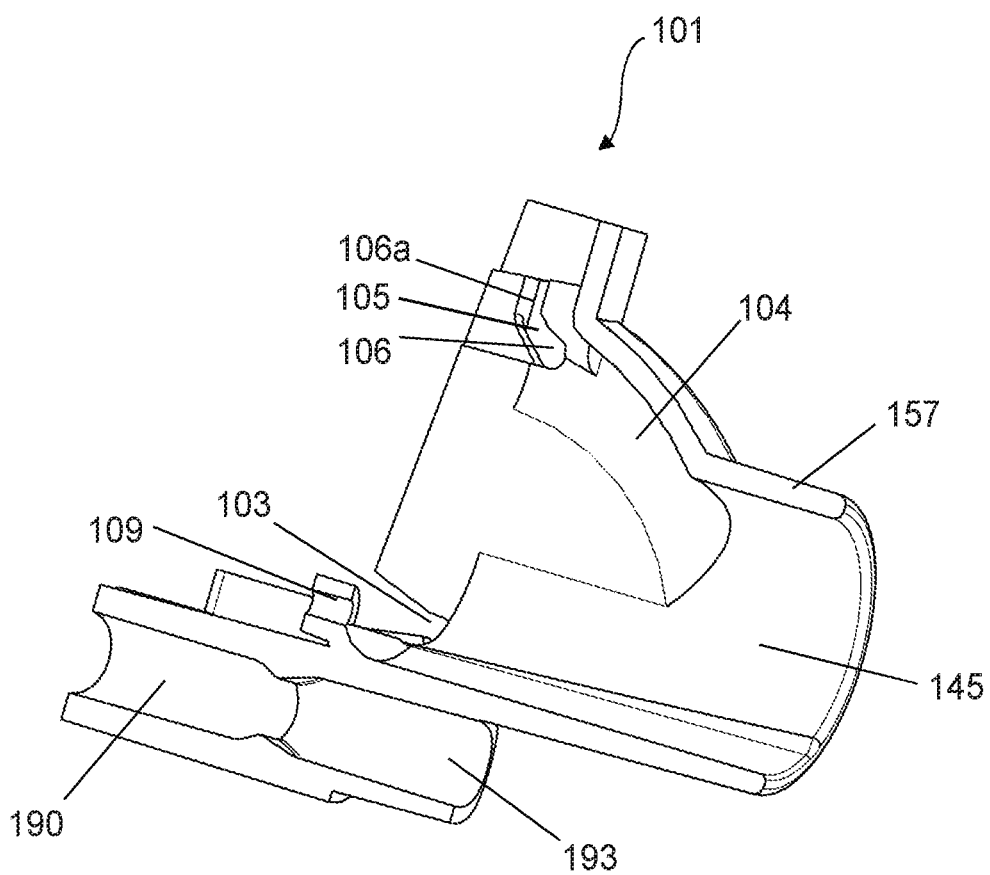
FIG. 5 is a side, partially cross-sectional, view of the trigger mechanism chassis of FIG. 2.

FIGS. 3-5 show the trigger mechanism chassis 101 shown in FIG. 2. The trigger mechanism chassis 101 comprises a hollow tube in the form of a mouthpiece 157 defining an air flow outlet 145, a wall providing a swept arc 104, toggle axle tracks 105 which define follow-through tracks 106 and primary tracks 106a, axle location features 103 and a flow governor passageway 190 with an inlet opening 193. The trigger mechanism chassis 101 also provides a sheath 109 to retain the end of a spring, and comprises two tubular location features 102. The trigger mechanism chassis 101 is preferably injection moulded from a plastic material.

Figure 6:
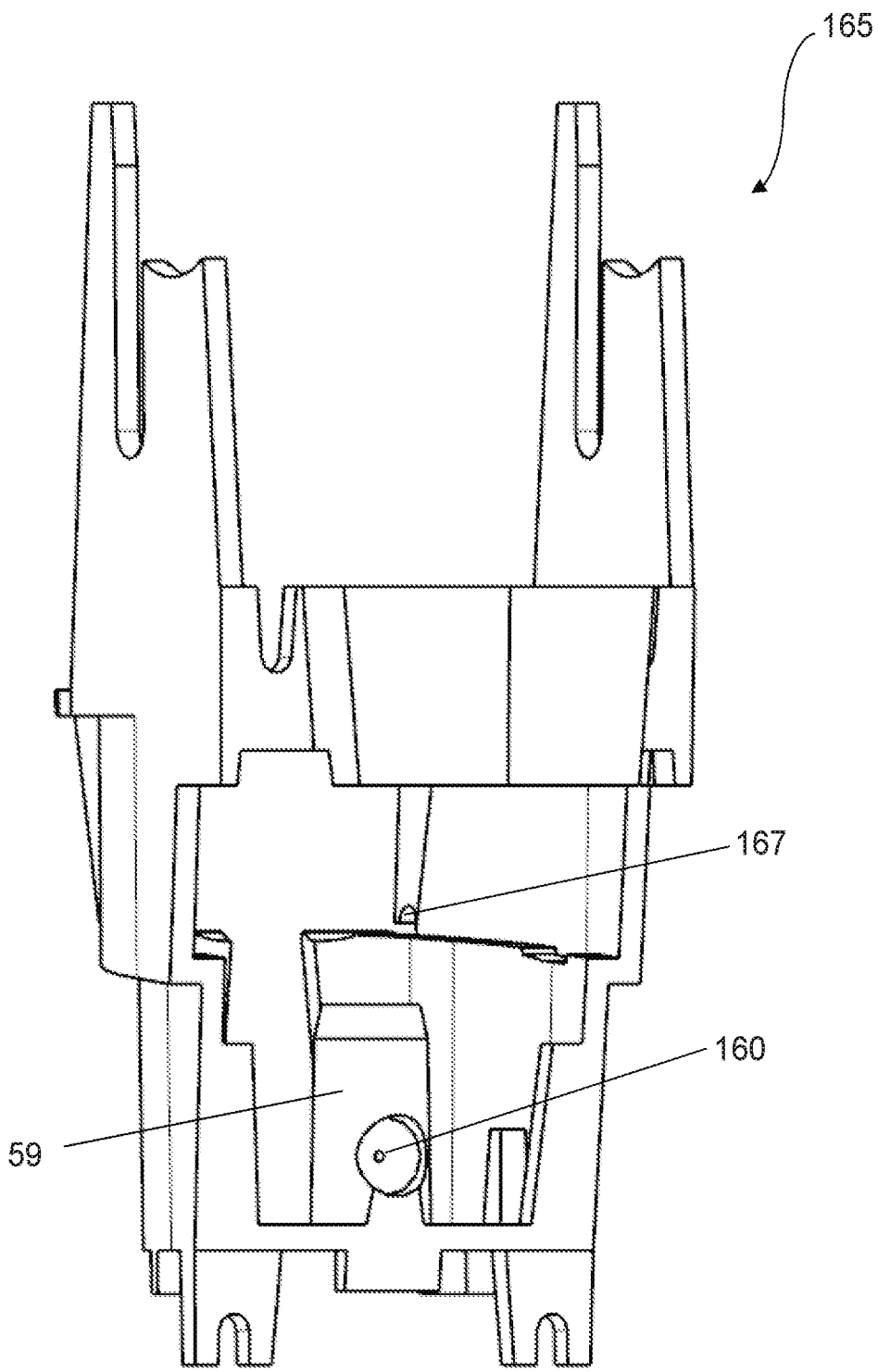
FIG. 6 is a front isometric view of the lower body component of FIG. 2.
Figure 7:
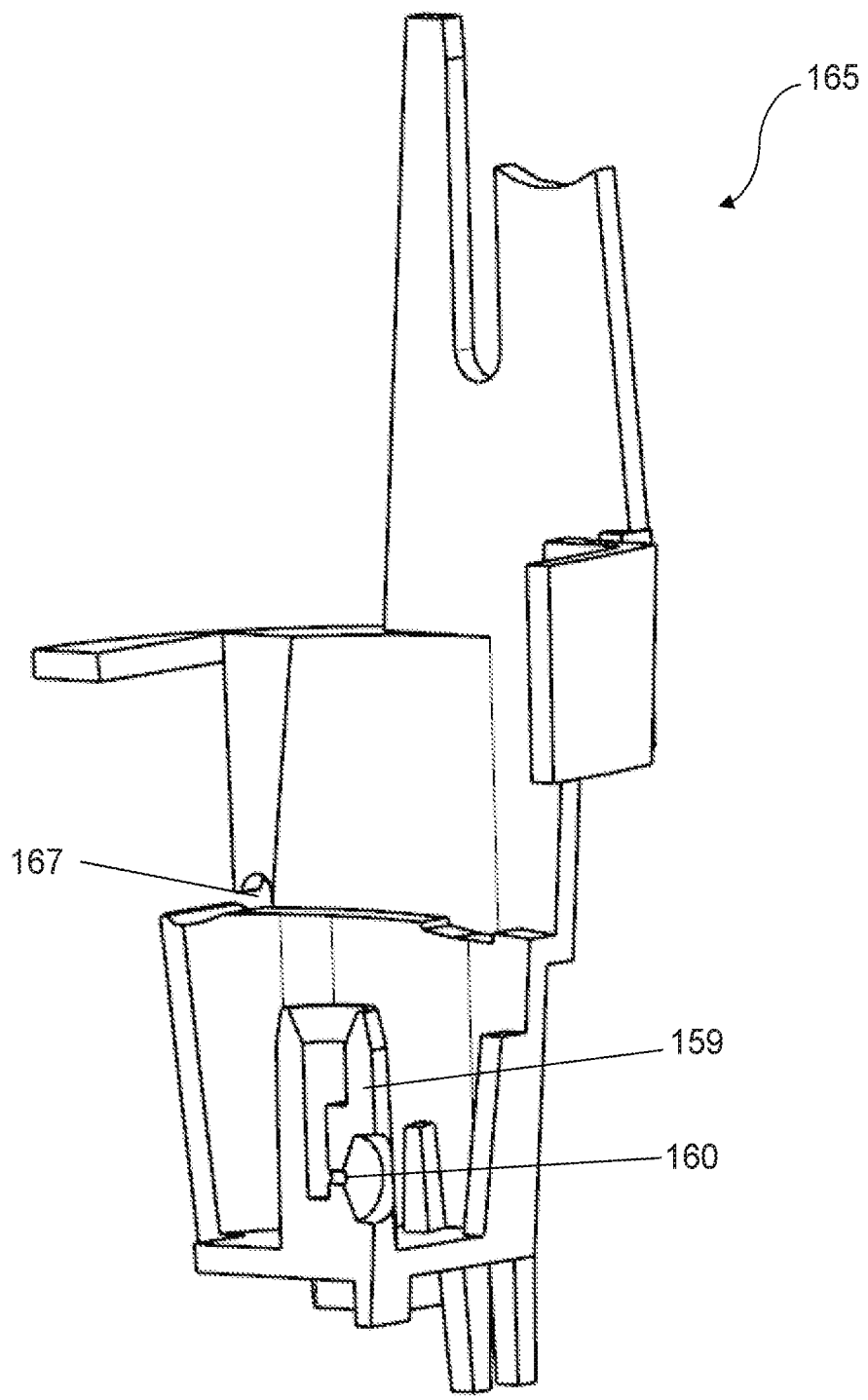
FIG. 7 is a front, partially cross-sectional, view of the lower body component of FIG. 2.
Figure 8:
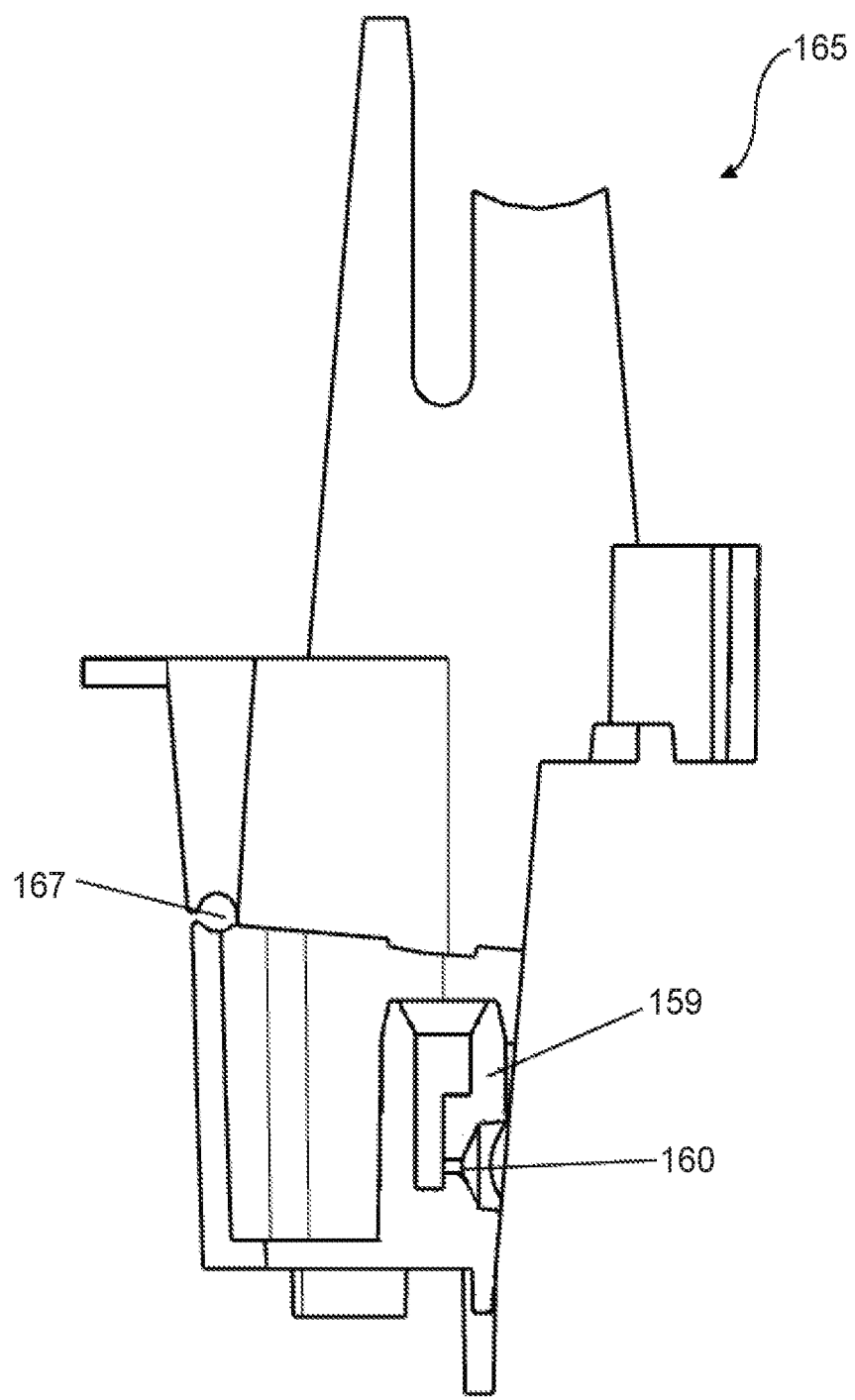
FIG. 8 is a side cross-sectional view of the lower body component of FIG. 2.

FIGS. 6-8 show the lower body component 165 shown in FIG. 2, comprising a stem socket 159 providing a spray orifice 160. The lower body component 165 also provides a chassis to support other components of the breath-actuated trigger mechanism. This includes bearings 167 to receive actuation arm pivots. The lower body component 165 is preferably injection moulded from a plastic material.

Figure 9:
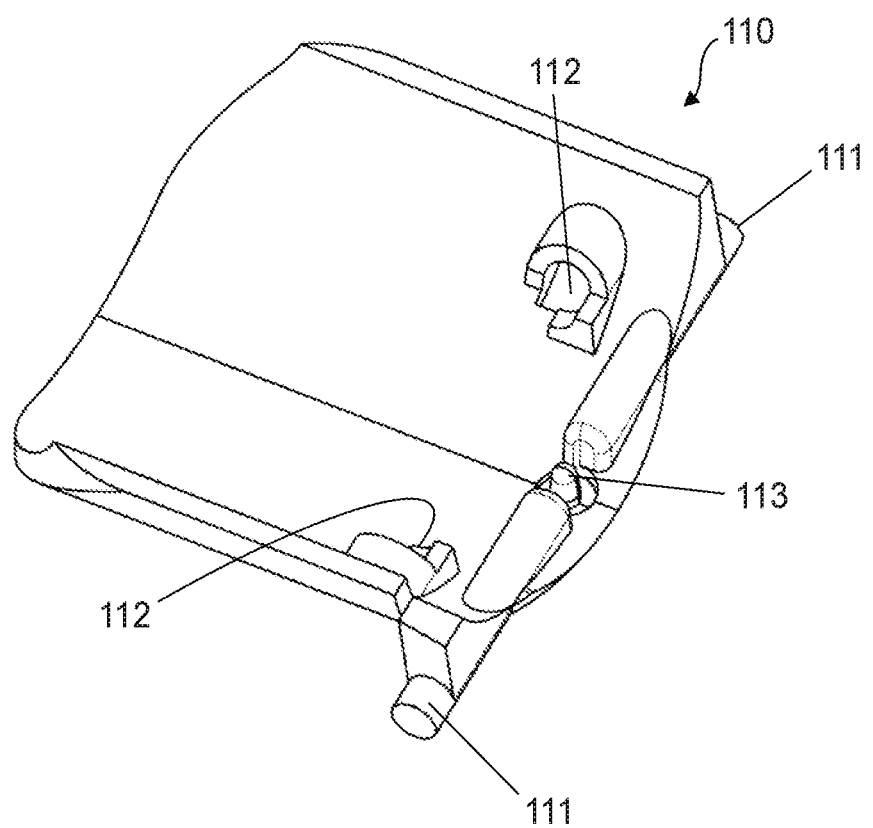
FIG. 9 is a rear isometric view of the vane of FIG. 2.

FIG. 9 shows the vane 110 shown in FIG. 2. The vane 110 comprises a curved vane wall with a vane pivot in the form of stub axles 111 at one end, and with toggle link pivot location features 112 formed some way along the vane wall from its end with the stub axles 111. The vane 110 also comprises a boss 113. The vane 110 is preferably injection moulded from a plastic material.

Figure 10:
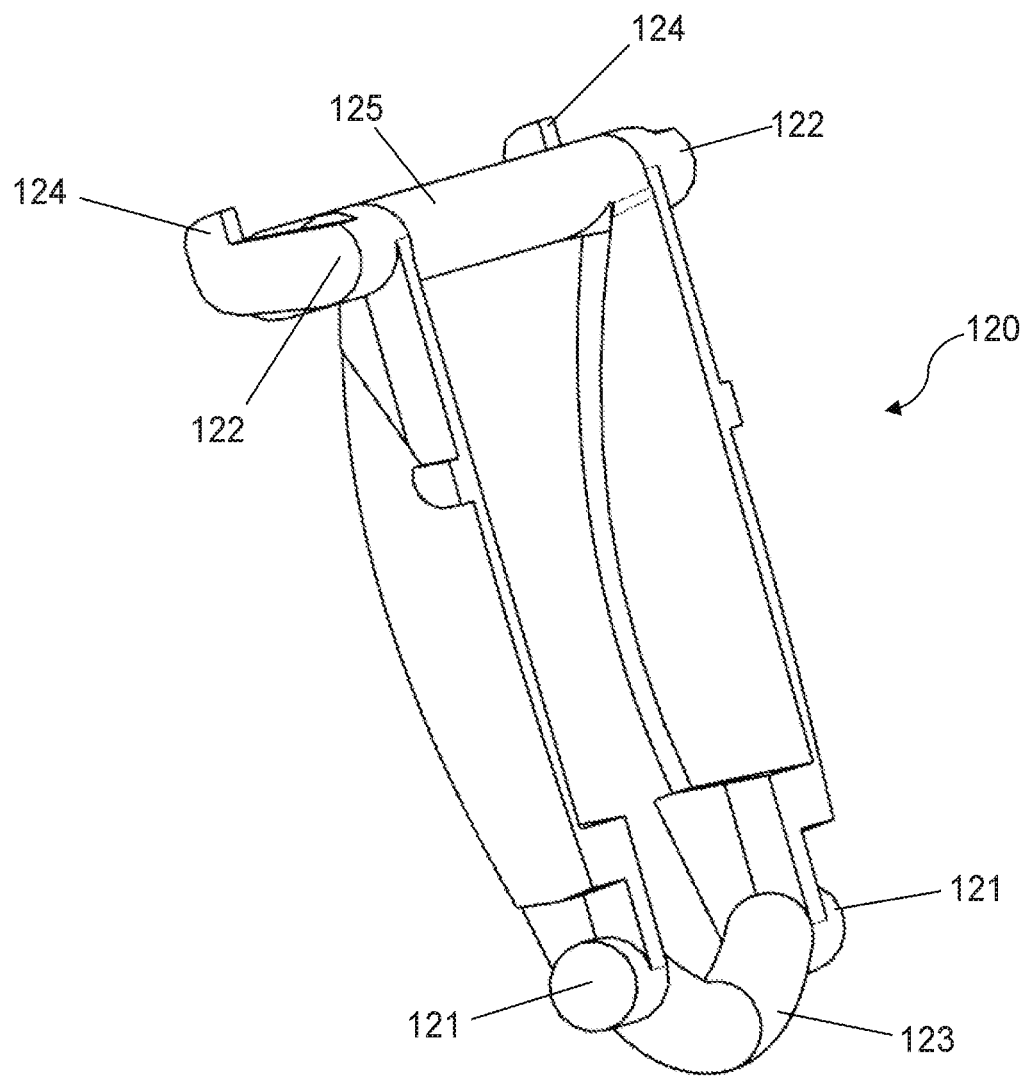
FIG. 10 is a rear isometric view of the toggle link of FIG. 2.

FIG. 10 shows the toggle link 120 shown in FIG. 2. The toggle link 120 is in the form of a generally rectangular frame, comprising two side walls linked at the top by an upper bar 125 and linked at the bottom by a lower bar 123. The upper bar 125 is curved forwards and extends outwards at each end beyond the rectangular frame, the outward extensions being in the form of stub axles 122 bearing bosses 124. The lower bar 123 is curved downwards and extends outwards at each end beyond the rectangular frame, the outward extensions being a toggle pivot in the form of stub pivots 121. The toggle link 120 is preferably injection moulded from a plastic material.

Figure 11:
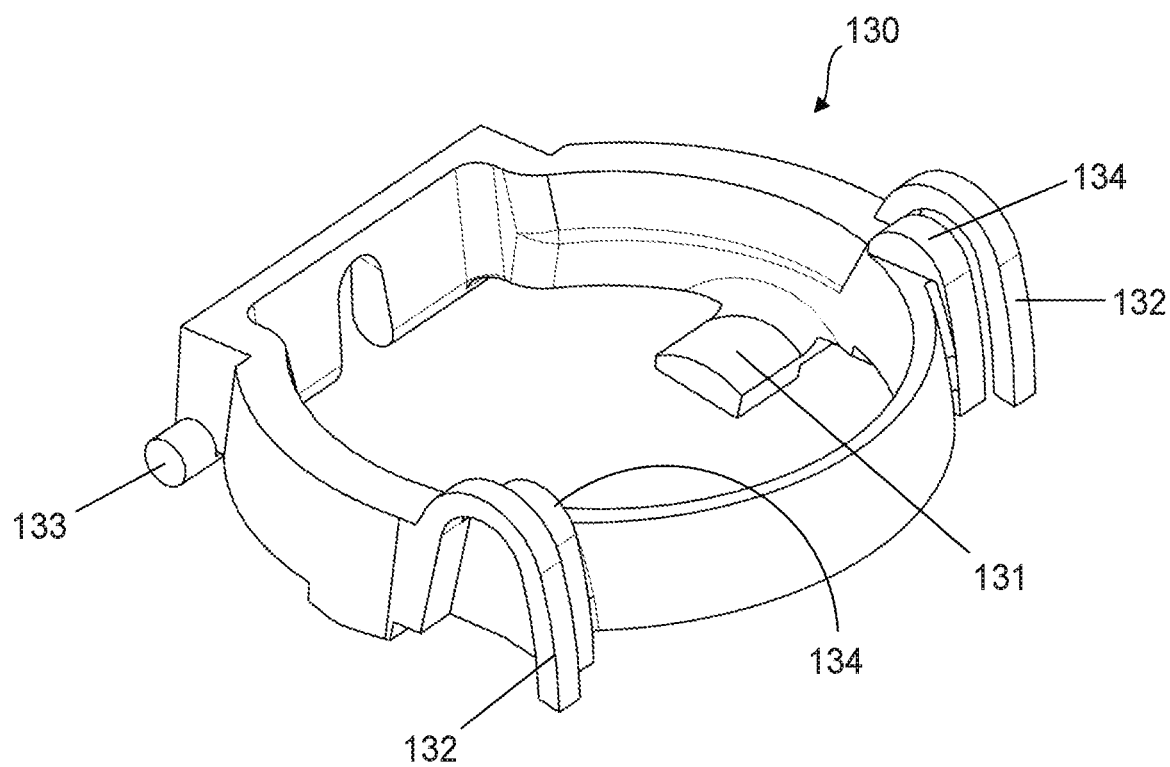
FIG. 11 is a top isometric view of the actuation arm of FIG. 2.

FIG. 11 shows the actuation arm 130 shown in FIG. 2. The actuation arm 130 is annular and bears two stub pivots 133 on one side, and two follow-through bosses 134 opposite them. Next to each boss 134 is an integral spring arm 132. On the inside edge of the annular ring, part way between the pivots 133 and the bosses 134 are two ledges 131. The actuation arm 130 is preferably injection moulded from a plastic material. To confer appropriate properties for the spring arm 132, the plastic material is preferably an acetal material.

Figure 12:
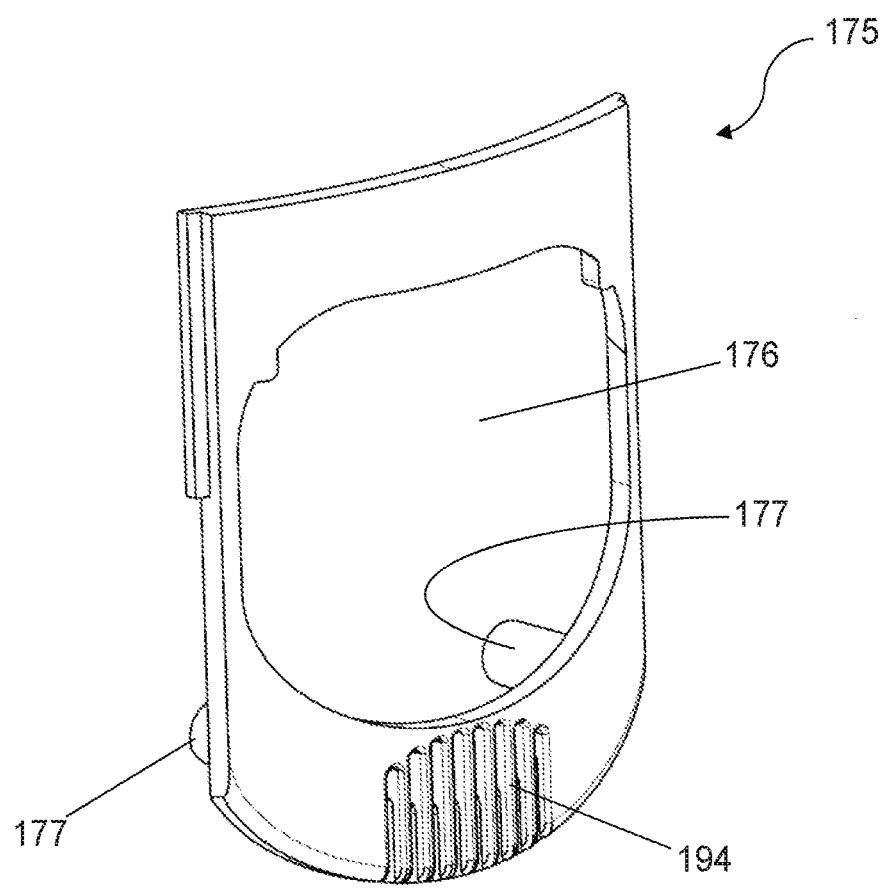
FIG. 12 is a front isometric view of the fascia component of FIG. 2.

FIG. 12 shows the fascia component 175 shown in FIG. 2. The fascia 175 comprises a generally flat plate comprising an aperture 176 to go over the mouthpiece 157. At its lower end, the fascia 175 comprises two location features 177 that can engage with the tubular location features 102 on the trigger mechanism chassis 101. The fascia 175 also forms a grill 194. The fascia component 175 is preferably injection moulded from a plastic material.

Figure 13:
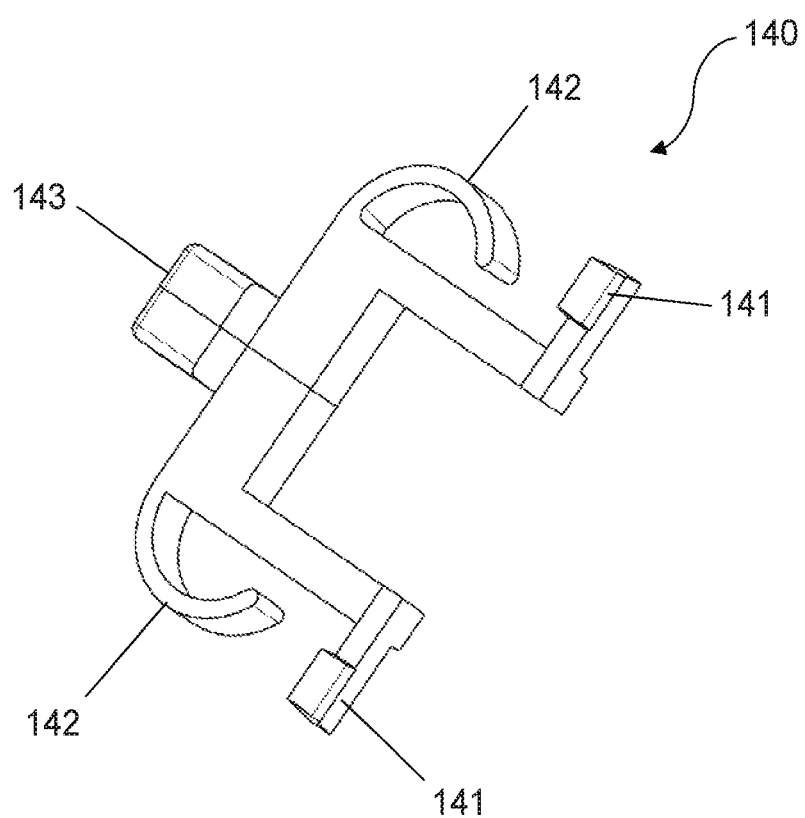
FIG. 13 is a top isometric view of the button component of FIG. 2.

FIG. 13 shows the button component 140 shown in FIG. 2. The button component 140 comprises a protruding button 143 at one end, and two contact features 141 at the other end.

The button component 140 also comprises two integral return spring arms 142. The button component 140 is preferably injection moulded from a plastic material. To confer appropriate properties to the spring arms 142, the plastic material is preferably an acetal material. The button component of FIG. 13 serves as an override feature that allows the patient to use the inhaler in a press-and-breathe mode, and may be used to prime the valve if required. In embodiments in which it is present, the override enables the patient to use it to press forward against the back of the toggle mechanism 119 (e.g., the back of the vane) to move the vane to an angle past its trigger point. When the valve is then actuated, the toggle mechanism 119 will already be in an unlocked position but will still be forced into the actuated position (with the vane against the floor of the mouthpiece). In other words, with the override button pressed the device will act similarly to a conventional press-and-breathe inhaler.

Figure 14:
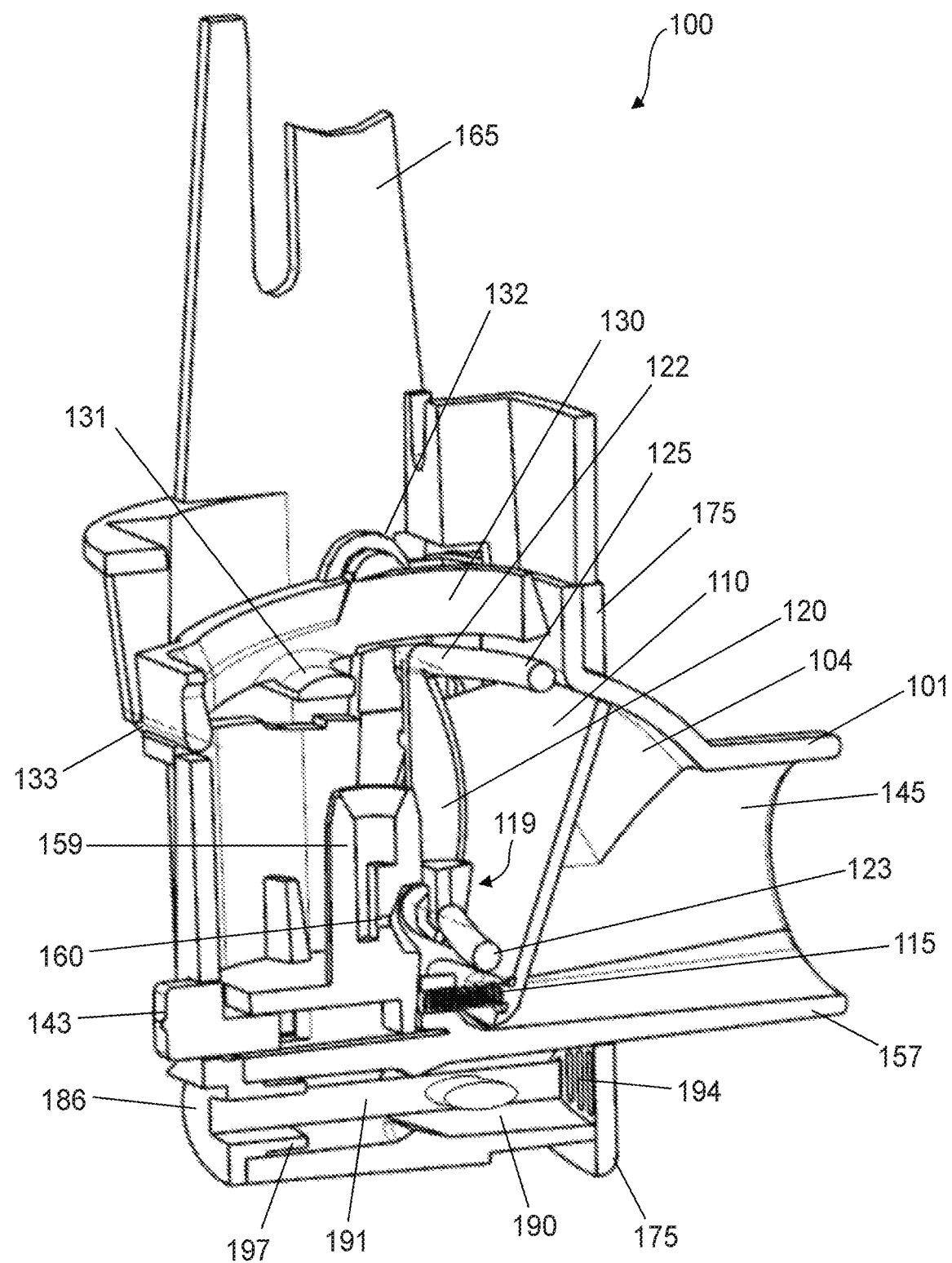
FIG. 14 is a side, partially cross-sectional, view of a breath-actuated trigger mechanism assembled from the components of the embodiment of FIG. 2, shown in its rest position.

FIG. 14 shows a breath-actuated trigger mechanism assembled from the components shown in FIG. 2, shown in its rest position. The trigger mechanism chassis 101 is attached to the lower body component 165, and the fascia 175 sits over the trigger mechanism chassis 101. The vane 110 is mounted within the trigger mechanism chassis 101, with the stub axles 111 engaged in the axle location features 103 of the trigger mechanism chassis 101 and with the vane's curved wall within the swept arc 104 of the trigger mechanism chassis 101. The toggle link 120 is also mounted within the trigger mechanism chassis 101, with its stub axles 122 in the toggle axle tracks 105 when the toggle link 120 is in its rest position, as shown in FIG. 14. The vane 110 and toggle link 120 form the toggle mechanism 119 as will be described in further detail shortly. The stub pivots 121 at the bottom of the toggle link 120 are engaged with the toggle link pivot location features 112 on the back of the vane 110, the engagement being in the form of a rotatable hinge. The vane spring 115 is a helical spring having a longitudinal axis of flexure. That is to say, the vane spring 115 has a centre line that runs along the centre of the helix from one end of the spring 115 to the other. That centreline (which need not be a straight line) defines the longitudinal axis along which the spring flexes. During flexing the shape of that longitudinal axis bends as the spring is loaded or unloaded. Thus, the primary reactionary force offered by the spring 115 results from longitudinal flexure rather than compression or extension of the spring along the line of the longitudinal axis. The spring 115 is mounted at a first end to the inside of the sheath 109 of the trigger mechanism chassis 101 and at a second end over the boss 113 on the vane 110. When the breath-actuated trigger mechanism of FIG. 14 is at rest, the spring 115 is slightly bent upwards in the centre by virtue of a deliberate misalignment between the boss 113 and the sheath 109. This bend provides a small residual spring force when the mechanism is at rest, this force increasing the stability of the at-rest (e.g., primed, ready to trigger) mechanism slightly.

The toggle mechanism 119 of FIG. 14 is designed not to go over-centre, but instead to be held by the friction generated in its stub axles 111 and stub pivots 121. It is also designed to hold back a significant load until the toggle mechanism is moved in a direction that pulls the vane stub axles 111 and toggle link 120 out of alignment. The friction in the toggle mechanism is overcome when the load, which is being held back by the toggle, can act with a significant resultant force in a direction that is close to perpendicular to the vane 110 and toggle link 120, i.e., when one of the links reaches a predetermined angle from its rest position. This angle will vary with the amount of friction in the overall mechanism.

In some breath-actuated trigger mechanisms of the present disclosure, the vane pivot in the form of stub axles 111 is located close to the stub pivots 121 of the toggle link 120 and the vane 110 pivots downwards towards the base of the mouthpiece. This allows the toggle link 120 to be designed in a way that allows the actuation arm 130 to continue past the toggle link 120 once the mechanism is in the actuated position. This follow-through is required to ensure that the pMDI valve can reach total travel, and greatly improves the mechanism's robustness to dimensional variations in the pMDI valve and canister. This follow-through ensures that the vane 110 is held against the base of the mouthpiece but allows an actuating arm to pass by it (i.e., that allows "follow-through") to dispense medicament.

In some embodiments of the present disclosure, the rest position of the vane 110 is set at an angle to help prevent airflow from leaking past the trigger mechanism. This also avoids any risk of clashing of the trigger mechanism with the vane 110, and therefore avoids adding unnecessary friction. At rest, the vane 110 provides a barrier to exhaled moisture and to bacteria and other undesirable entities in the exhaled breath: this is advantageous to protect the main parts of the inhaler should the patient unadvisedly exhale into it.

In its actuated position, the vane 110 sits against the base of the mouthpiece. In some embodiments, the vane has been given a specific profile that allows it to sit against the floor of a conventional mouthpiece when actuated, yet to provide sufficient resistance to the airflow whilst in the rest position.

In use, the actuation arm 130 is used to transmit the patient force from the pMDI valve's ferrule to the trigger mechanism. The actuation arm 130 prevents the valve from firing until the toggle mechanism is actuated. The actuation arm 130 contacts the ferrule approximately half way along its length and engages the toggle link 120 at its other end. This configuration results in reduction in the force (from the patient) that is applied to the toggle mechanism, giving an approximate additional mechanical advantage of 2:1. The actuation arm also has a spring arm attached to it which acts against the actuator and provides sufficient force to return the actuation arm 130 after actuation.

The vane 110 and toggle link 120 are returned to their rest positions after firing by the spring 115.

Figure 15:
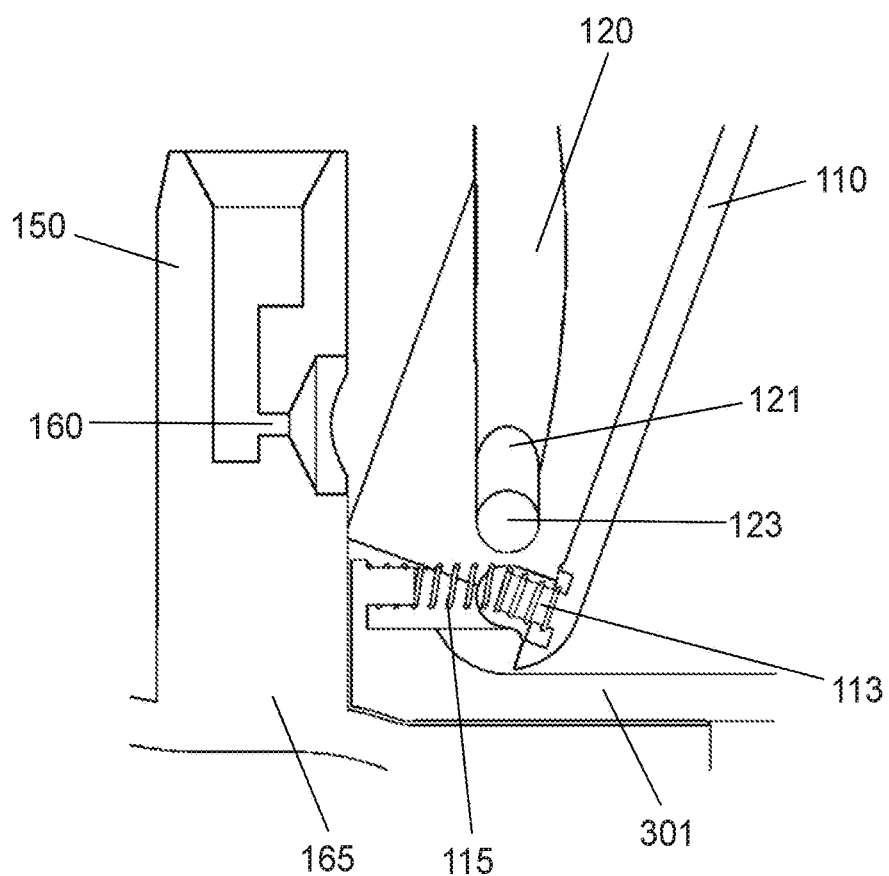
FIG. 15 is a partial, schematic, view of part of an alternative embodiment of the breath-actuated trigger mechanism of the present disclosure, shown in its rest position.

FIG. 15 shows the spring 115 in more detail. (FIG. 15 shows a slightly different embodiment of the breath-actuated trigger mechanism than that shown in FIG. 14, in which the spring 115 is mounted on two bosses rather than between one boss and one sheath.) A benefit of this configuration is that it takes up little space and hence tends to ensure that the spring is not directly in the path of the spray plume.

To ensure that the spring will return the mechanism reliably, a bending pre-load force is imposed on it. A pre-load ensures that the mechanism will reset even at worst case component dimensional tolerances or if the device friction were to increase slightly due to wear or the presence of drug, dirt or moisture. The bend in the spring 115 at rest, and hence its stabilising pre-load that tends to bias the vane towards its upright at-rest position, can be observed in FIG. 15. Using a conventional helical compression spring in this side-loaded configuration—or, alternatively, a helical tension spring (not shown)—provides a low and relatively constant force that can be used to reset the mechanical pMDI breath-actuated trigger mechanism.

In other applications, springs used to provide a low and relatively constant force can be coiled strips of spring steel.

The main disadvantages of such springs are that they are difficult to handle and assemble and that they can take up a lot of room. Use of the side-loaded helical springs of embodiments of the present disclosure provides a spring with similar force features but without the impact on assembly and space. Using a low, consistent force vane return spring allows a low force to trigger the breath-actuated trigger mechanism, making it more suitable for patients with limited lung function. A greater vane return force would increase the inhalation pressure required for the patient to trigger the mechanism to release a breath-actuated dose. The spring does need to provide enough force to guarantee reset of the mechanism, but the design of the mechanism is such that only lifting the mass of the mechanism components against gravity is required. The spring force thus needs to be small, but needs to be reliable. Side loading (bending) of a compression or tension spring results in a relatively constant force curve, and such an arrangement is used to return preferred embodiments of pMDI breath-actuated trigger mechanisms of the present disclosure.

In embodiments incorporating a compression spring, care must be taken to ensure that the spring is not loaded axially, as this would cause the vane to tend to open rather than close. The length of the spring must be considered throughout the full motion of the mechanism. A spring that increases in length as it is bent could add unwanted excessive load to the vane, which would increase the triggering force and/or prevent the vane's return after the cessation of inhalation.

Figure 16:
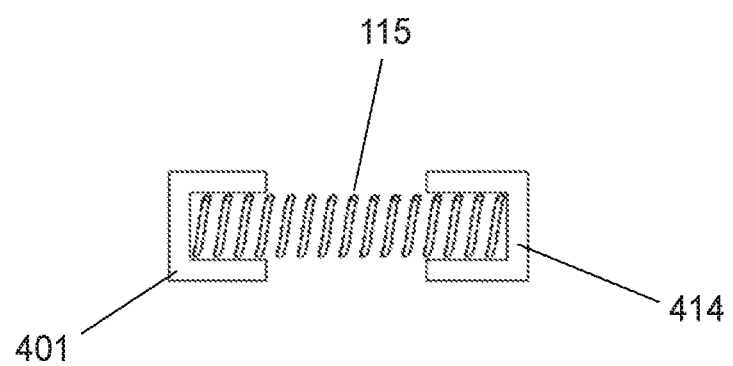
FIG. 16 is a partial, schematic, view of part of a further embodiment of the breath-actuated trigger mechanism of the present disclosure.

FIG. 16 shows a further alternative configuration around the spring 115, in which both ends are located in shroud features 401, 414. The shroud features are preferably moulded onto the chassis and the vane respectively. Again, the spring 115 is preferably held in a slightly bent configuration at rest, by relative positioning of the shrouds 401, 414 in the primed position of the trigger mechanism. In embodiments of the present disclosure, one end of the spring 115 is held in a sheath on the trigger mechanism chassis 101 and the other end is located on a part of the mechanism that needs to be returned (e.g., on the vane 110, or the toggle link 120). In such embodiments, the sheathing elements apply load to the outer diameter of the spring. To ensure that the spring is not plastically deformed, it must have a sufficient unsupported length between the sheaths. The required unsupported length rises (e.g., approximately proportionately) to the angle through which the spring is being bent, and also is dependent on the diameter and properties of the spring.

In other embodiments of the present disclosure, the spring 115 may be attached by both ends to a component of the trigger mechanism, e.g., one end to the toggle link and the other end to the vane. Where the components of the trigger mechanism, including the vane, are interconnected, return of such connected components to their primed conditions results in the vane being returned to its primed condition.

As shown in FIG. 14, the actuation arm 130 is mounted in the lower body component 165, the stub pivots 133 of the former being rotatably mounted in the bearings 167 of the latter. The front of the actuation arm 130 rests on the upper end of the toggle link 120 when the mechanism is at rest, with the spring arms 132 contacting ledges on the lower body component. In use, canister 51 (not shown in FIG. 14) is placed into the mechanism 100, with the tip of its stem portion 58 engaging with the stem socket 159, and with the underside of its metering valve 54 contacting the two ledges 131 on the actuation arm 130. At rest, as shown in FIG. 14, the mechanism 100 is stable, with the toggle linkage supporting the load that the patient applies to the canister's base 149.

Figure 17:
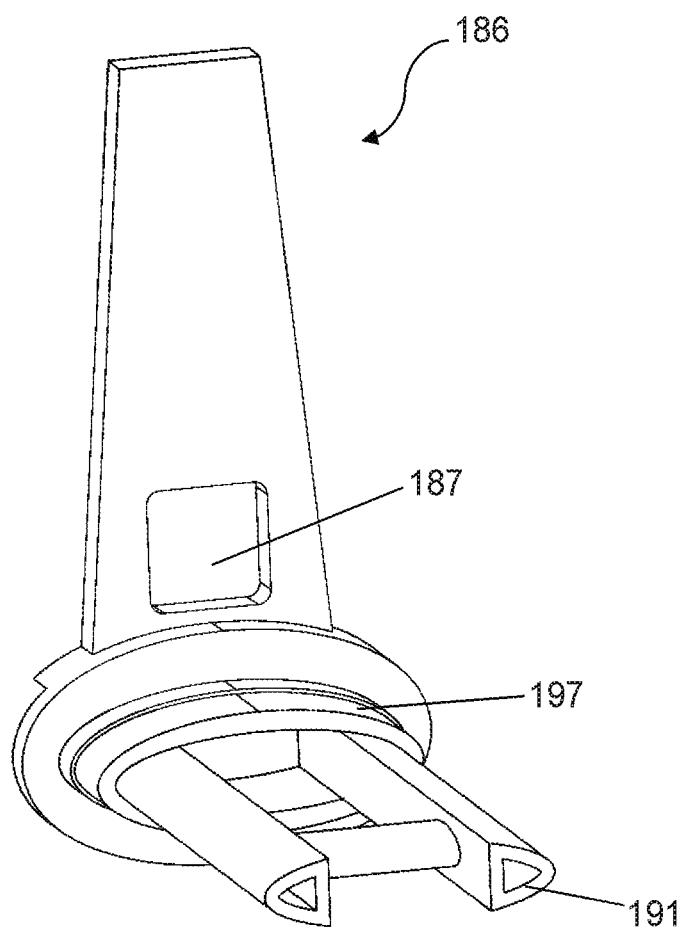
FIG. 17 is a front isometric view of the flow governor support component of FIG. 2.

FIG. 17 shows the flow governor support component 186 shown in FIG. 2. The flow governor support component 186 comprises an oval base 197 on which a collapsible silicone tube flow governor component (not shown) can be mounted. Such an assembly can form the basis of a known flow governor mechanism with the internal support structure of the flow governor mechanism being provided by support features 191 formed on the flow governor support component 186. Additionally, the flow governor support feature extends upwards at its back into a wall with an aperture 187 in it. When the flow governor support component 186 is assembled on to the lower body component 165, as shown in FIG. 14, this aperture 187 provides a location for the button 143 to protrude for access by the patient. (FIG. 14 shows the button component 140 pre-assembled into the mechanism.)

Figure 18:
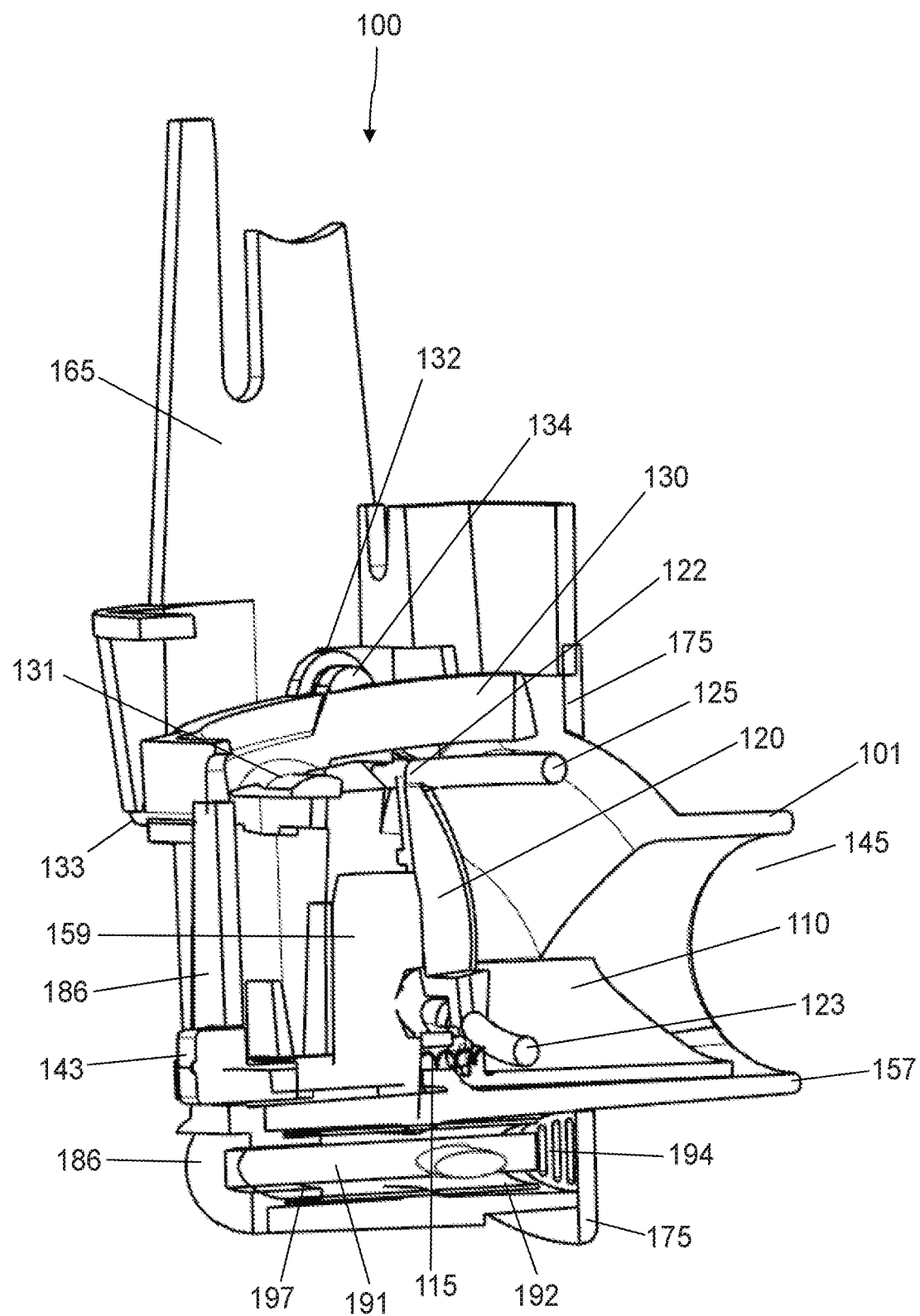
FIG. 18 is a side, partially cross-sectional, view of the breath-actuated trigger mechanism of FIG. 14, with the addition of a flow governor tube component, shown in its actuated position.
Figure 19:
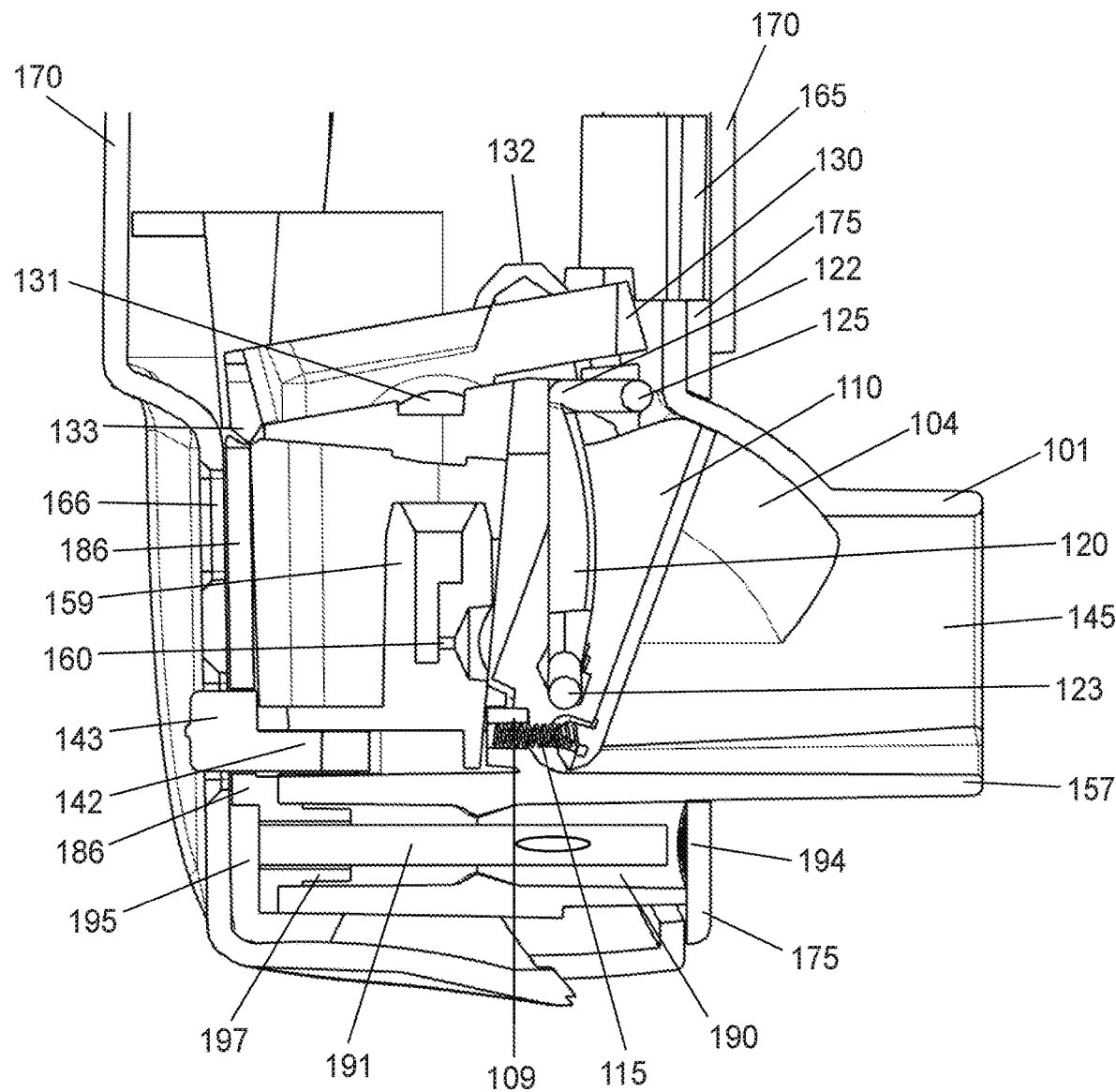
FIG. 19 is a side, partially cross-sectional, view of the breath-actuated trigger mechanism of FIG. 14, fitted into a housing, shown in its rest position.

FIG. 18 shows the mechanism 100 of FIG. 14, but with the addition of a flow governor tube component 192, shown in its actuated position following patient inhalation through the mouthpiece 157. As the patient inhales, air passes outwardly through the air outlet 145, causing a pressure drop across the curved wall of the vane 110. This pressure drop causes the vane 110 to rotate, clockwise as drawn in FIG. 18, with its stub axles 111 rotating in the axle location features 103 of the trigger mechanism chassis 101. As the vane 110 rotates, the toggle link pivot location features 112 on the back of the vane 110 are displaced towards the open end of the mouthpiece 157. This displacement pulls the stub pivots 121 of the toggle link 120 sideways, thus unlatching the toggle linkage and overcoming the small restoring force from the vane spring 115. With a pre-load applied to the base 49, and thence through the canister 51 and its metering valve 54 onto the actuation arm 130 and onto the toggle link 120, e.g., by downwards pressure applied manually by the patient on the base 49, the toggle linkage collapses, with the toggle link 120 moving generally downwards. The movement of the toggle link 120 is steered by its stub pivots 121 being pulled round by the rotational displacement of the toggle link pivot location features 112, and by its stub axles 122 following the toggle axle tracks 105. As the canister continues to move downwards under the applied (e.g., patient-applied) load, the actuation arm 130 in turn pushes the toggle link 120 down until its stub axles 122 leave the primary tracks 106a of the toggle axle tracks 105 and pass into their curved lower portions, i.e. into the follow-through tracks 106. The forwardly curved nature of these causes the stub axles 122 (and thence the top end of the toggle link 120) to move forward, out of the way of the actuation arm 130. This allows the actuation arm 130 to move downwards far enough to allow movement of the canister 51 as far as the total travel of the stem portion 58 into the metering valve 54. Hence, even in cases of extreme component dimensional tolerances, the valve stem 58 is allowed to move far enough to release a dose of aerosolised medicament formulation. In other words, the mechanism 100 allows "follow-through" of valve motion after its triggering point. Note that the two follow-through bosses 134 obstruct the stub axles 122 and thus hold the toggle link 120 down, thereby preventing the toggle link 120 and the vane 110 from being reset by the vane spring 115 until the load has been removed from the ledges 131 (e.g. when the load has been released from the canister by the patient). The two follow-through bosses 134 also serve to ensure that the toggle cannot ride over the top of the actuation arm 130 and thence wedge it down.

FIG. 19 shows the breath-actuated trigger mechanism of FIG. 14, fitted into a housing 170, shown in its rest position. The housing component 170 provides an outer shell into which the breath-actuated trigger mechanism fits. It provides a more attractive, and ergonomic form for the patient, and it provides protection for the mechanism inside. At its rear it has a window opening 166, and below that it has another opening through which the protruding button 143 on the button component 140 can protrude. This button 143 serves as a manual override: if a patient for any reason wishes to take a dose manually, rather than in breath-actuated fashion, then pressing on the button 143 causes the contact features 141 to push against the back of the vane 110, causing the vane to start to rotate as if breath actuated. The load on the canister 51, e.g., manually applied by the patient to the base 49 of the canister 51, causes the toggle linkage to collapse further to allow dose release as has been described above.

Figure 20:
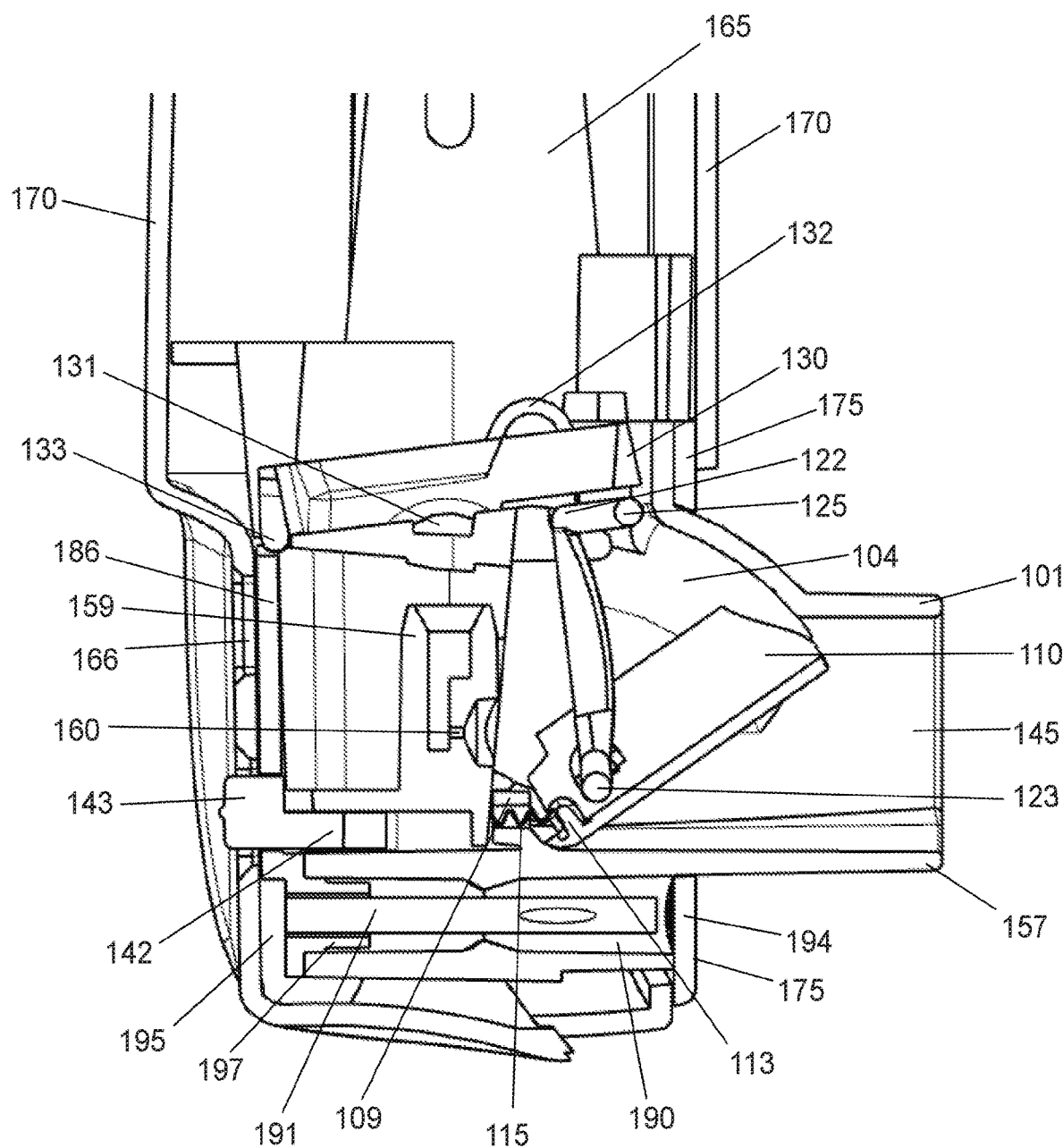
FIG. 20 is a side, partially cross-sectional, view of the breath-actuated trigger mechanism of FIG. 19, shown in a partially fired position.

FIG. 20 shows the breath-actuated trigger mechanism of FIG. 19, shown in a partially fired position. As can more clearly be seen from this FIG., the forward rotation of the vane 110 pulls the lower end of the toggle link 120 out of its previous stable alignment between the lower end of the vane 110 and its own upper end.

Figure 21:
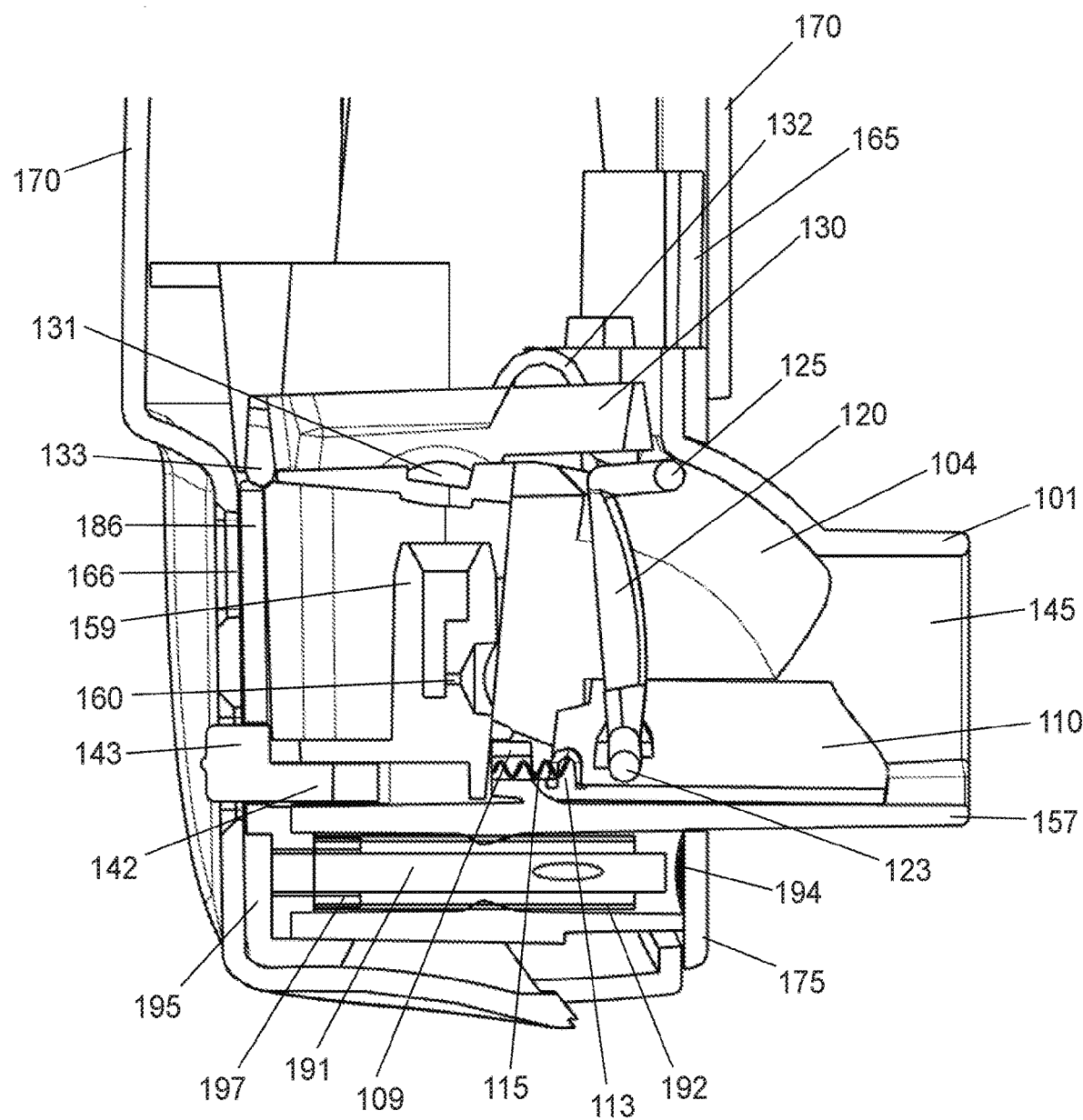
FIG. 21 is a side, partially cross-sectional, view of the breath-actuated trigger mechanism of FIG. 19, with the addition of a flow governor tube component, shown in its fired position.

FIG. 21 is a side, partially cross-sectional, view of the breath-actuated trigger mechanism of FIG. 19, with the addition of a flow governor tube component, shown in its fired position. In other words, it is very similar to FIG. 18, but with the addition of the housing 170.

Figure 22:
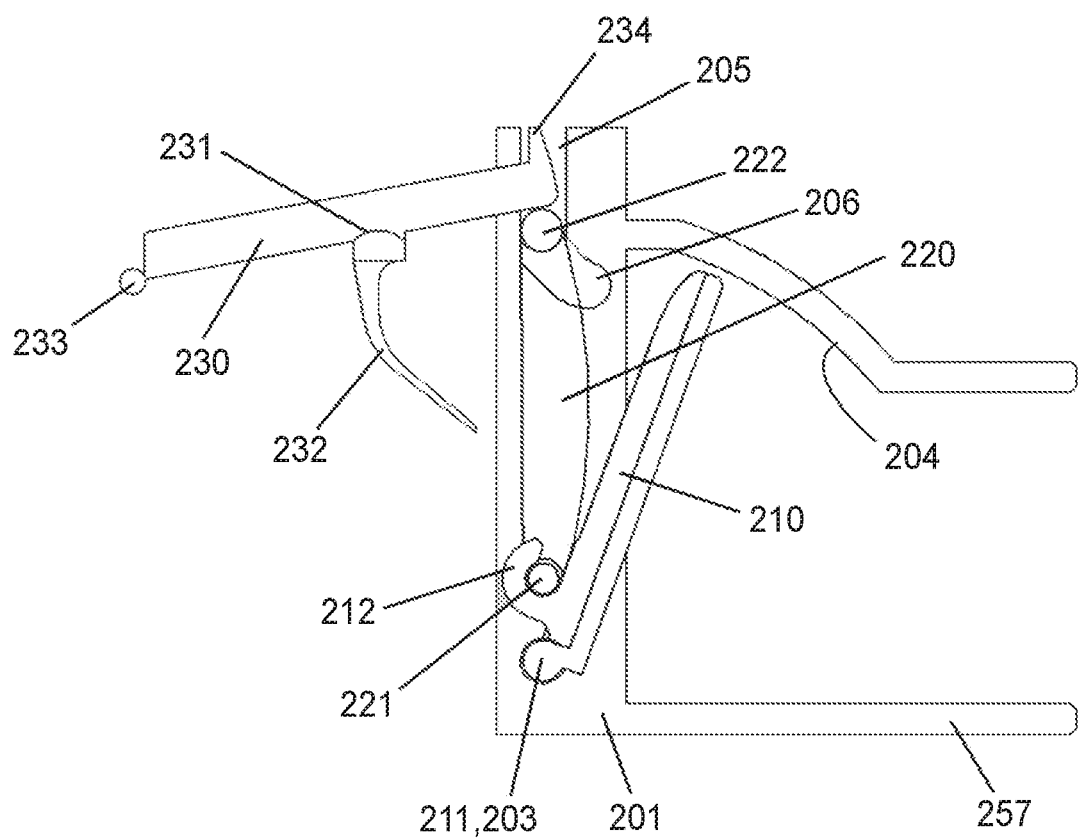
FIG. 22 is a schematic, partially cross-sectional, view of part of yet another embodiment of the breath-actuated trigger mechanism of the present disclosure, shown in its rest position.

FIG. 22 is a schematic, partially cross-sectional, view of part of yet another embodiment of the breath-actuated trigger mechanism of the present disclosure, shown in its rest position. Because the figure is a schematic, somewhat simplified depiction of the mechanism, it serves to illustrate more clearly some of the aspects of some embodiments of the present disclosure. The figure shows a vane 210, mounted by stub axles 211 rotatable in fixed location features 203 in a trigger mechanism chassis 201, and comprising a mouthpiece 257, such that the end of the vane's curved wall can sweep out the arc surface 204 of the trigger mechanism chassis 201. The vane 210 bears hinge location features 212 that engage with the bottom stub pivots 221 of a toggle link 220 to form a rotational hinge point. At the opposite, top, end of the toggle link 220 is a pair of upper stub axles 222 that run in tracks formed in the trigger mechanism chassis 201. At rest, as shown in FIG. 22, the stub axles 222 sit in straight regions of the tracks 205, aligned approximately parallel with the toggle link 220. Further down, towards the toggle's hinge, however, the tracks curve forwards towards the swept arc region 204, forming "follow-through" tracks 206. Above the top of the toggle link 220 sits an actuation arm 230, pivoted at a pivot 233 at its distal end and bearing a pair of return spring arms 232, of different form to those in previously described embodiments, and a pair of ledges 231 to locate the underside of a metering valve (not shown) and to resist any downwards force on it when the mechanism is in the rest position shown in FIG. 22.

At rest, because of the stable nature of the toggle linkage arrangement of FIG. 22, made slightly more stable by the presence of a vane spring (not shown in FIG. 22), the entire breath-actuation trigger mechanism of this embodiment is stable yet sensitive.

Figure 23:
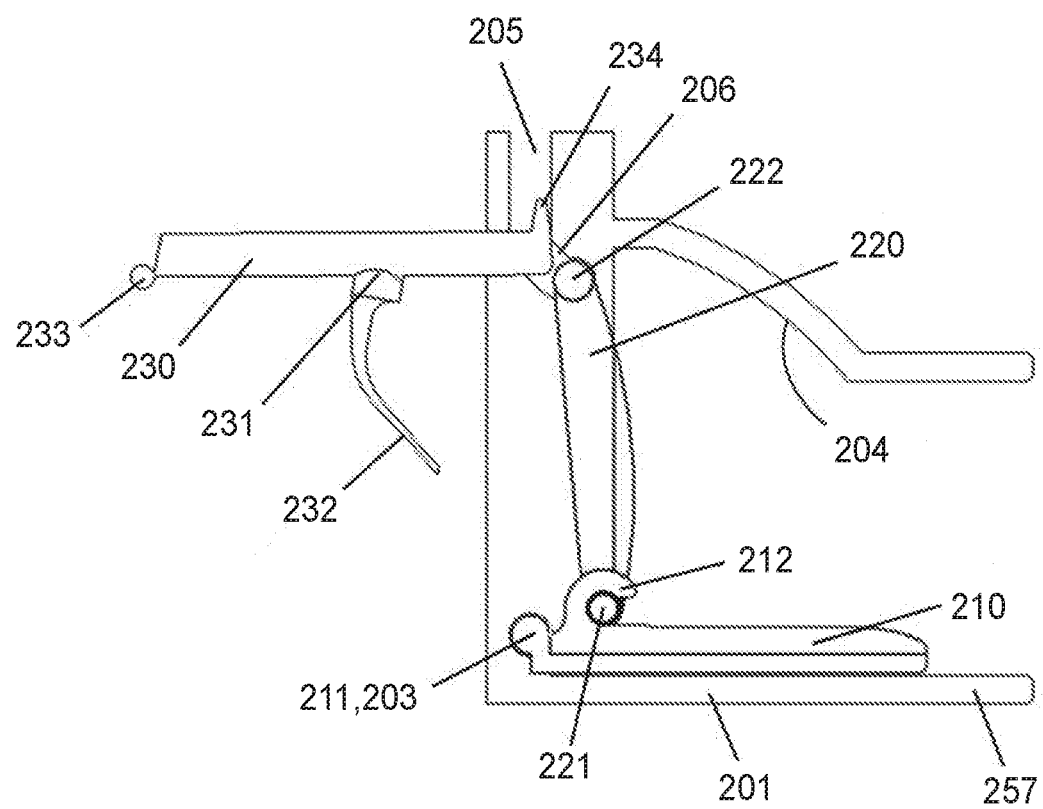
FIG. 23 is a schematic, partially cross-sectional, view of the breath-actuated trigger mechanism of FIG. 22, shown in its fired position.

FIG. 23 is a schematic, partially cross-sectional, view of the breath-actuated trigger mechanism of FIG. 22, shown in its fired position. As can be seen by comparison with FIG. 22, the vane 210 has rotated downwards (clockwise from FIG. 22 to FIG. 23) against the floor of the mouthpiece 257 under the influence of a patient's inhaled breath. In consequence of that rotation, the hinge location features 212 have pulled the bottom stub pivots 221 slightly towards the mouthpiece 257, pulling the bottom end of the toggle link 220 slightly forward and down. That movement in turn pulls the upper stub axles 222 down the straight toggle tracks 205 and into the forward-curving tracks 206, thereby pulling the top of the toggle link 220 out of the rotational arc of the actuation arm 230. With the toggle linkage no longer supporting the load applied via ledges 231 to the actuation arm 230, it is free to rotate downwards (clockwise, as shown in FIG. 23), thereby allowing the pMDI canister (not shown) to move downwards to release a dose of medicament spray.

A key feature of the mechanisms of this disclosure is the fact that the actuating arm components (e.g., 130, 230) can "follow through" past the actuation position. This allows the valve to reach its "total travel" position and is less sensitive to variation in valve firing points and tolerances. To further ensure that each valve is able to reach its "total travel", two "follow-through" bosses 134, 234 are formed on top of the free end of the actuation arm 130, 230.

Figure 24:
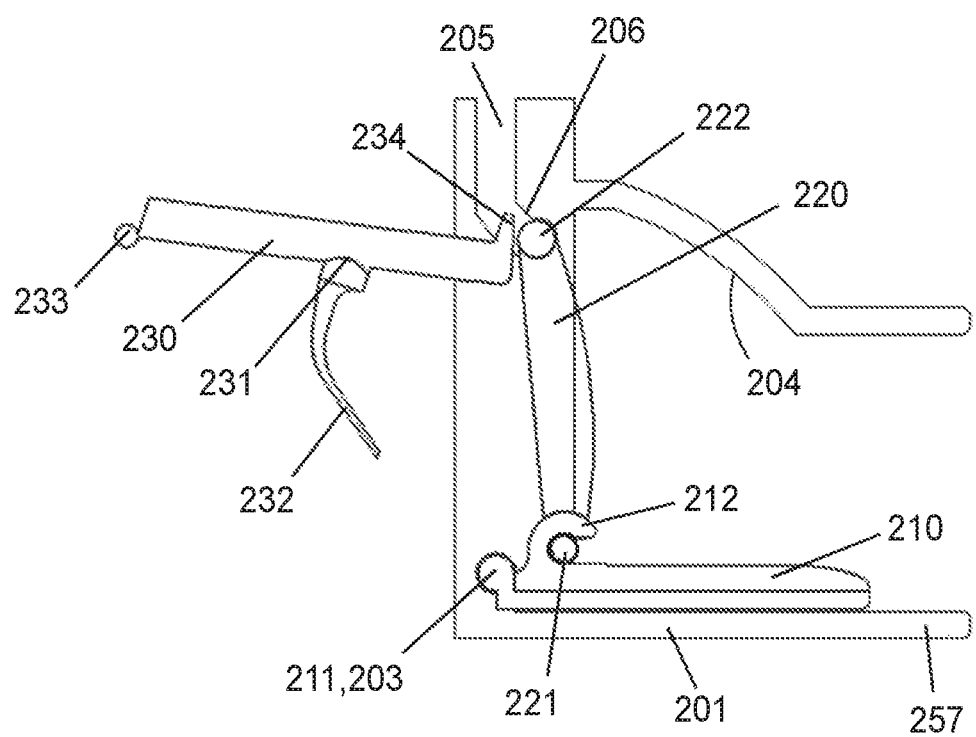
FIG. 24 is a schematic, partially cross-sectional, view of the breath-actuated trigger mechanism of FIG. 22, shown in its follow-through position.

FIG. 24 is a schematic, partially cross-sectional, view of the breath-actuated trigger mechanism of FIG. 22, shown in its follow-through position. The two follow-through bosses 234 can clearly be shown to obstruct the upper stub axles 222, thereby preventing them from travelling back up their tracks 206, 205 until the reset sequence is initiated.

Reset of the mechanism occurs as follows. The first step is that the load is removed from the base 49 of the canister 51, for example either by the patient unloading a firing spring (not shown) in a fully-automated breath-actuated inhaler or by the patient ceasing to press downwards on the base 49 of the pMDI canister 51 (e.g., in embodiments of this disclosure). Removing the load from the pMDI canister allows the return spring in the metering valve 54 to reset the valve and allows the spring arms 132 to return the actuation arm 130 to its rest position. As the follow-through bosses 134 move back upwards with the actuation arm 130, the stub axles 122 are able to move back up their toggle axle tracks 106, 105 as the vane spring 115 resets the toggle link 120 and the vane 110. The toggle linkage is thus reset.

It will be appreciated by the skilled person that it is possible to construct an embodiment similar to that in FIGS. 22 to 24, but with the trigger mechanism inserted the other way up. In other words, the stub axles of the vane sit in the tracks; while the stub axles are located in axle location features. In such a construction, the movement of the vane is more complicated since its pivot axis moves in an arc.

It will be appreciated that the breath responsive inhaler of the disclosure may be a dry powder inhaler, particularly one where the dose is dispensed by releasing an energy source to the powder, upon activation of a trigger mechanism by the patient's inhalation.

Figure 25:
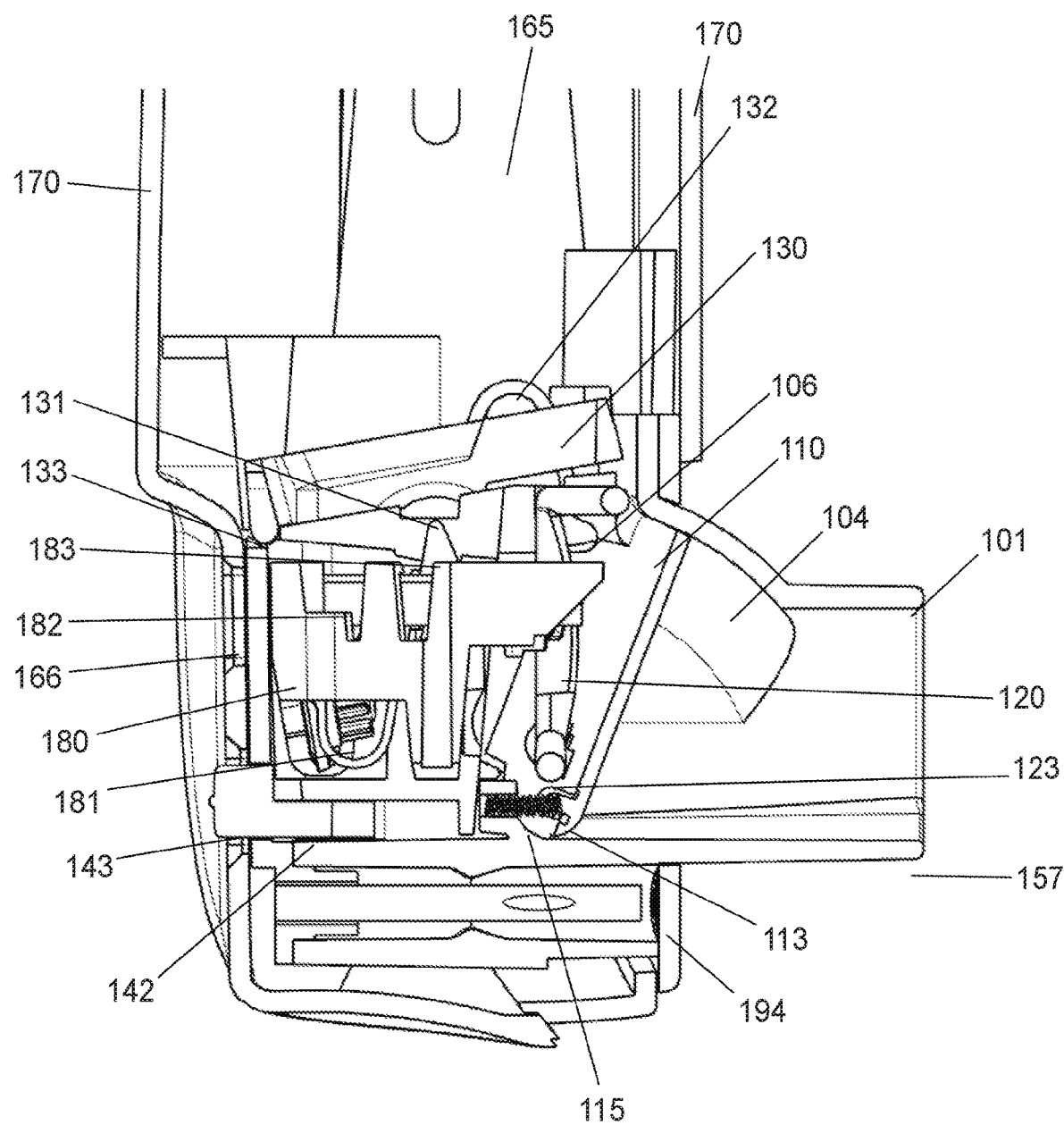
FIG. 25 is a side, partially cross-sectional, view of the breath-actuated trigger mechanism of FIG. 19, with the addition of a dose counter mechanism, shown in its rest position.

Another desirable feature of some preferred embodiments of the trigger mechanisms of this disclosure is that they are compatible with mechanical dose counters, such as those disclosed in WO2015/006292, incorporated herein in its entirety by reference. FIG. 25 is a side, partially cross-sectional, view of the breath-actuated trigger mechanism of FIG. 19, with the addition of a dose counter mechanism, shown in its rest position. The dose counter mechanism comprises three components: a chassis component 180, a units cone component 181, and a tens ring component 182. A full description of this exemplary dose counter and its operation is provided in WO2015/006292. In this embodiment of the present disclosure, the dose counter is located around the stem socket 159 (not readily discernible in FIG.

25). It is operated by contact of the undersides of the ledges 131 of the actuation arm 130 with the upwardly protruding features 183 on the moving part of the dose counter chassis component 180 (see FIG. 25 and also WO2015/006292).

Preferably, the trigger mechanisms of the current disclosure are configured and manufactured to have low friction, thereby improving their triggering sensitivity.

It is to be understood that the embodiments of the present invention is not limited in its application to the details of construction and the arrangement of components set forth in the above description or illustrated in the accompanying drawings. The invention is capable of other embodiments and of being practiced or of being carried out in various ways. Also, it is to be understood that the phraseology and terminology used herein is for the purpose of description and should not be regarded as limiting. It is to be further understood that other embodiments may be utilized, and structural or logical changes may be made without departing from the scope of the present disclosure.

The embodiments described above and illustrated in the figures are presented by way of example only and are not intended as a limitation upon the concepts and principles of the present disclosure. As such, it will be appreciated by one having ordinary skill in the art that various changes in the elements and their configuration and arrangement are possible without departing from the spirit and scope of the present disclosure.

All references and publications cited herein are expressly incorporated herein by reference in their entirety into this disclosure.

Various features and aspects of the present disclosure are set forth in the following claims.

The invention claimed is:

1. A breath-responsive metered dose inhaler having a trigger mechanism for triggering delivery of a medicament and a trigger mechanism chassis for locating the trigger mechanism within the inhaler,
the trigger mechanism including:
a breath responsive member moveable upon inhalation of the user from a primed position in which the inhaler is prevented from delivering medicament, to a triggered position in which the medicament is delivered to the user,
a spring having a longitudinal axis, configured to be flexible along the longitudinal axis, and comprises a pre-load bend along the longitudinal axis when the breath responsive member is in the primed position,
wherein the spring is configured to bias the breath responsive member from the triggered position towards the primed position by flexure along the longitudinal axis of the spring.

2. The inhaler according to claim 1, in which the spring is a helical spring.

3. The inhaler according to claim 2, in which the flexure is a straightening flexure.

4. The inhaler according to claim 3, in which the trigger mechanism comprises a toggle mechanism comprising the breath responsive member, wherein the helical spring is attached to the toggle mechanism.

5. The inhaler according to claim 4, in which the helical spring has a first end attached to the breath responsive member and a longitudinally opposing second end attached to the trigger mechanism chassis.

6. The inhaler according to claim 5, in which the helical spring is constrained by the trigger mechanism chassis, and the helical spring comprises a further bend giving rise to an increased biasing force in the triggered position.

7. The inhaler according to claim 6, in which the helical spring is attached to the trigger mechanism chassis by an interference fit of the second end of the helical spring inside a sleeve of the trigger mechanism chassis or outside a boss of the trigger mechanism chassis.

8. The inhaler according to claim 7, in which the helical spring is attached to the breath responsive member by an interference fit of the first end of the helical spring inside a sleeve of the breath responsive member or outside a boss of the breath responsive member.

9. The inhaler according to claim 8, in which, during return of the breath responsive member from the triggered position to the primed position, the helical spring undergoes substantially no compression or tension along its longitudinal axis.

10. The inhaler according to claim 9, in which the breath responsive member is constrained to pivot about a fixed axis and the helical spring engages the breath responsive member close to the fixed axis.

11. The inhaler according to claim 10 in which the breath responsive member is constrained to pivot about the fixed axis and the helical spring acts as a live pivot so as to define the fixed axis.

12. The inhaler according to claim 11 in which the breath responsive member is a vane.

13. The inhaler according to claim 12 which is a pressurized metered dose inhaler.

* * * * *